US008849398B2

(12) United States Patent
Evans

(10) Patent No.: US 8,849,398 B2
(45) Date of Patent: *Sep. 30, 2014

(54) EXPANDABLE BLOOD PUMP FOR CARDIAC SUPPORT

(71) Applicant: Minnetronix, Inc., St. Paul, MN (US)

(72) Inventor: Don W. E. Evans, St. Paul, MN (US)

(73) Assignee: Minnetronix, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/840,019

(22) Filed: Mar. 15, 2013

(65) Prior Publication Data
US 2013/0303831 A1 Nov. 14, 2013

Related U.S. Application Data

(63) Continuation-in-part of application No. 13/590,488, filed on Aug. 21, 2012, now Pat. No. 8,734,331, which is a continuation-in-part of application No. 13/590,564, filed on Aug. 21, 2012.

(60) Provisional application No. 61/528,536, filed on Aug. 29, 2011, provisional application No. 61/528,536, filed on Aug. 29, 2011.

(51) Int. Cl.
*A61N 1/00* (2006.01)
*A61M 1/12* (2006.01)
*A61M 1/10* (2006.01)

(52) U.S. Cl.
CPC ........... *A61M 1/101* (2013.01); *A61M 1/125* (2014.02); *A61M 1/1024* (2014.02); *A61M 1/1034* (2014.02); *A61M 1/1032* (2014.02)

USPC .......................................... 607/16

(58) Field of Classification Search
USPC .......................................... 607/16
See application file for complete search history.

(56) References Cited

U.S. PATENT DOCUMENTS

| 4,105,016 A | 8/1978 | Donovan, Jr. |
| 4,753,221 A | 6/1988 | Kensey et al. |

(Continued)

FOREIGN PATENT DOCUMENTS

| EP | 2 229 965 | 9/2010 |
| EP | 2 338 541 | 6/2011 |

(Continued)

OTHER PUBLICATIONS

International Search Report and Written Opinion mailed on Dec. 7, 2012 in connection with International Patent Application No. PCT/US2012/052031. 13 pages.

(Continued)

*Primary Examiner* — Robert N Wieland
(74) *Attorney, Agent, or Firm* — Kenneth E. Levitt; Dorsey & Whitney LLP

(57) ABSTRACT

A pump for inducing flow within a vascular system comprises two inlets. The pump has a first configuration for deployment within the vascular system and a second, operable configuration for directing the fluid flow within the vascular system, where the second configuration has a greater diameter than the first configuration. A centrifugal impeller is configured to induce the fluid flow by rotation about an axis of rotation, where the flow is in a direction generally transverse to the impeller's axis of rotation.

20 Claims, 29 Drawing Sheets

(56) References Cited

U.S. PATENT DOCUMENTS

| | | |
|---|---|---|
| 6,533,716 B1 | 3/2003 | Schmitz-Rode et al. |
| 6,827,682 B2 | 12/2004 | Bugge et al. |
| 6,974,436 B1 | 12/2005 | Aboul-Hosn et al. |
| 6,981,942 B2 | 1/2006 | Khaw et al. |
| 7,027,875 B2 | 4/2006 | Siess et al. |
| 7,070,555 B2 | 7/2006 | Siess |
| 7,638,915 B2 | 12/2009 | Sentmanat |
| 7,841,976 B2 | 11/2010 | McBride et al. |
| 7,878,967 B1 | 2/2011 | Khanal |
| 7,942,804 B2 | 5/2011 | Khaw |
| 8,371,997 B2 * | 2/2013 | Shifflette .................. 600/16 |
| 2006/0245959 A1 | 11/2006 | LaRose et al. |
| 2008/0103591 A1 | 5/2008 | Siess |
| 2008/0114339 A1 | 5/2008 | McBride et al. |
| 2008/0132747 A1 * | 6/2008 | Shifflette .................. 600/16 |
| 2008/0132748 A1 | 6/2008 | Shifflette |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2010/0191035 A1 | 7/2010 | Kang et al. |
| 2011/0009687 A1 | 1/2011 | Mohl |
| 2011/0071338 A1 | 3/2011 | McBride et al. |
| 2011/0106120 A1 | 5/2011 | Haselby et al. |
| 2013/0066140 A1 | 3/2013 | McBride et al. |

FOREIGN PATENT DOCUMENTS

| | | |
|---|---|---|
| WO | 03/103745 | 12/2003 |
| WO | 2010/042546 | 4/2010 |
| WO | 2010/105854 | 9/2010 |
| WO | 2010133567 A1 | 11/2010 |
| WO | 2011/035926 | 3/2011 |
| WO | 2011/089022 | 7/2011 |

OTHER PUBLICATIONS

International Search Report and Written Opinion mailed on Dec. 12, 2012 in connection with International Patent Application No. PCT/US2012/052034. 14 pages.

International Search Report and Written Opinion for PCT Application No. PCT/US2014/021752, mailed Jul. 17, 2014. (10 pages).

* cited by examiner

EXPANDABLE BLOOD PUMP FOR CARDIAC SUPPORT

CROSS-REFERENCE TO RELATED APPLICATIONS

This application is a Continuation-in-Part application of U.S. patent application Ser. No. 13/590,488, filed Aug. 21, 2012, entitled "EXPANDABLE BLOOD PUMPS AND METHODS OF THEIR DEPLOYMENT AND USE," which claims priority to U.S. Provisional Application No. 61/528,536, filed Aug. 29, 2011. This application is also a Continuation-in-Part application of U.S. patent application Ser. No. 13/590,564, filed Aug. 21, 2012, entitled "EXPANDABLE VASCULAR PUMP," which claims priority to U.S. Provisional Application No. 61/528,536, filed Aug. 29, 2011. The content of each of the above-referenced applications is hereby incorporated by reference herein in their entirety.

BACKGROUND

The present disclosure relates to blood pumps for cardiac support. More particularly, the present disclosure relates to expandable blood pumps and methods of their deployment and use for circulatory support. A variety of cardiac problems result in the need for temporary cardiac support. These scenarios can range from contingency support during high risk cardiac surgery to immediate full support after a myocardial infarction. Acute pumps for temporary cardiac support differ from implantable pumps because the period of use may be measured short-term, in days or weeks, rather than long-term months or years. Situations requiring temporary cardiac support can benefit strongly from quick deployment of a blood pump in a range of anatomical locations.

The blood pumps of the present disclosure have application in different aspects of the cardiovascular system. The body's cardiovascular system is a closed loop system, which consists of two types of circulation, pulmonary circulation and systemic circulation. In pulmonary circulation, blood flows from the right portion of the heart through the pulmonary trunk, which branches into pulmonary arteries, which carry the blood flow to the lungs. In the lungs, blood flows through pulmonary capillaries, where carbon dioxide is removed from, and oxygen added to, the blood. The oxygenated blood then flows to the left portion of the heart, where it is pumped through the aorta to flow throughout the body. The pumping of oxygenated blood throughout the body is known as systemic circulation. In systemic circulation, the left side of the heart pumps blood through the aorta and into the arterial system, which carries the blood throughout the body, to capillaries, and to the body's cells. As the oxygenated blood flows through the body, the cells of the body remove the oxygen from the blood and replace it with carbon dioxide. The blood then enters the venous system, to begin its return trip to the heart and lungs. The venous system contains venules, which converge into veins. In the body's upper section, blood flows from the veins into the superior vena cava, while in the lower section of the body, the blood flows from the veins into the inferior vena cava. Blood flows from the superior vena cava and from the inferior vena cava into the right atrium of the right heart, where it reenters the cycle of pulmonary circulation.

Because blood flows from the right portion of the heart and into the lungs, while blood that flows from the left portion of the heart is circulated throughout the body, the left heart generates substantially higher pressure than the right heart. The pressure generated by the right heart would not be sufficient to move blood throughout the body's tissues, while the pressure generated by the left heart, if applied to blood that circulates through the lungs, would damage the fragile alveoli tissue in the lungs. In general, the right heart generates systolic pressures of 15-30 mm Hg and diastolic pressures of 3-8 mm Hg, while the left heart generates systolic pressures of 100-140 mm Hg and diastolic pressures of 3-12 mm Hg.

There exists a need in the art for blood pumps that can improve aspects of this type of therapy. More specifically, there is a need in the art for improved expandable blood pumps for cardiac support, and further, for cardiac support for the left portion of the heart, the right portion of the heart, or both.

SUMMARY

This disclosure relates to a pumping system for inducing flow within a vascular system, and methods for using the pumping system to induce such flow. The system includes a cannula having a section that is adjustable between an operable configuration and a deployment configuration, and an impeller positioned within the adjustable section. The system includes at least one end with an expandable member that is adapted to engage with a blood vessel. The system is configured to move blood from at least one end and through a side wall of the cannula.

BRIEF DESCRIPTION OF THE DRAWINGS

While the specification concludes with claims particularly pointing out and distinctly claiming the subject matter that is regarded as forming the various embodiments of the present disclosure, it is believed that the embodiments will be better understood from the following description taken in conjunction with the accompanying Figures, in which:

FIG. 7A is a side schematic view of the cannula embodiment of FIG. 6 in an expanded configuration.

FIG. 7B is an end schematic view of the cannula embodiment of FIG. 6 in the expanded configuration.

FIG. 11A is a side schematic view of an opening in a wall between any combination of heart chamber(s) and blood vessel(s).

FIG. 11B is a side schematic view of the cannula embodiment of FIG. 10A fixed within the opening of FIG. 11A.

DETAILED DESCRIPTION

Figure 1:
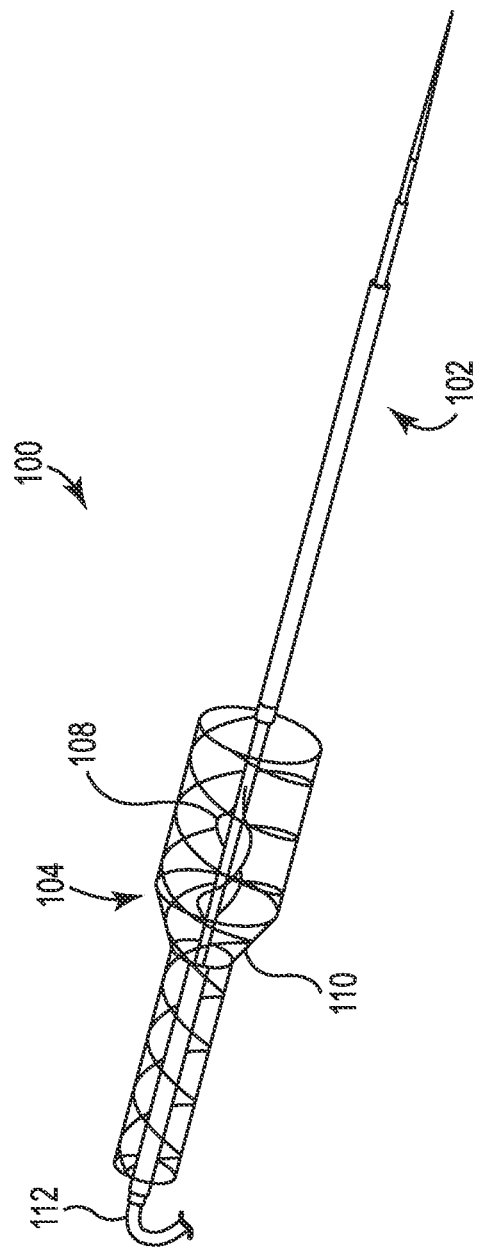
FIG. 1 is a perspective view of an expandable blood pump according to one embodiment of the present disclosure.

The present disclosure relates to novel and advantageous blood pumps for cardiac support, including but not limited to acute cardiac support and temporary cardiac support. Particularly, the present disclosure relates to novel and advantageous expandable blood pumps and methods of their deployment and use for quickly providing temporary circulatory support. The systems of the present disclosure can be used in the left portion of the heart, the right portion of the heart, or both. Example uses of the various embodiments of expandable blood pumps provided herein can range from contingency support during high risk cardiac surgery to immediate full support after a myocardial infarction. Expandable blood pumps and methods of their deployment and use for circulatory support are described in U.S. application Ser. No. 13/590,488 to Evans et al., filed Aug. 21, 2012, entitled Expandable Blood Pumps and Methods of their Deployment and Use, and U.S. application Ser. No. 13/590,564, filed Aug. 21, 2012, entitled Expandable Vascular Pump, both of which are incorporated by reference herein in their entireties.

In general, a pump, with a cannula and impeller in a collapsed, deployment configuration, may be inserted into, for example, a major blood vessel and guided to the heart. Once the pump is placed in or near the desired location, e.g., desired portion and chamber of the heart, the clinician or operator may use catheter controls to expand the pump's cannula. With the cannula expanded and a conduit created, the clinician or operator may then expand the pump's impeller within the cannula; alternately, expansion of cannula and impeller may occur at the same time.

Rotation of the impeller generates blood flow within the cannula between the cannula's inlet and outlet or outlets. The cannula may also provide separation between any surrounding tissue and the rotating impeller. The cannula also may be adapted to engage with structure or tissues in the heart, such as blood vessels, including the vena cavea, such as the superior vena cava, the inferior vena cava, other vessels, or combinations of these. The impeller may be driven via a power transmission system and controlled from a control and/or power unit. The clinician or operator may enter therapeutic system parameters into the control unit, which drives the pump at desired speeds for desired periods of time. The collapsed, deployment configuration may permit quick insertion to, and removal from, several anatomical positions while the expanded, operable configuration may permit appropriate therapy.

The present disclosure, in one embodiment, relates to expandable blood pumps and methods of their deployment and use for circulatory support. The blood pump may include a cannula constructed of an adjustable support member and flexible mesh cover allowing a deployment configuration of reduced or minimum collapsed size and an operable configuration of increased or maximum expanded size.

In another embodiment, the cannula may vary in diameter along its axial length reducing or minimizing the interference between the expanded cannula and tissue openings. In addition, cannula diameter variation can allow for a leading narrow portion of the cannula which can improve maneuverability and permit an increased reach in anatomy. Further yet, cannula diameter variation can allow for fixing the position of the pump with respect to a vessel opening or other port that it passes through.

The cannula may include multiple openings, which can assist in preventing zero flow if a tissue collapses at the inlet end of the cannula. The cannula, in some embodiments, may be configured such that an outlet ejects flow generally perpendicularly to the pump's axis of rotation. The blood pump may be powered by a fluid system including catheter supply and return channels that cause a mechanical generator to rotate. The mechanical generator may be mechanically or magnetically coupled to an impeller of the blood pump.

The present disclosure, in another embodiment, relates to a pump for inducing motion of a fluid relative the pump. The pump may include an elongated cannula having at least one section adjustable between an operable configuration having a first diameter and a deployment configuration having a substantially smaller diameter.

The pump may also include an impeller positioned within the adjustable section of the cannula and rotatable therein about an impeller axis. The impeller can include a rigid or semi-rigid mast or flexible support member supporting a flexible web, the mast or support member being separately positionable with respect to the cannula between an operable configuration and a deployment configuration, the operable configuration extending at least a portion of the web to a first radial distance from the impeller axis and the deployment configuration collapsing the portion of the web to a second radial position of substantially shorter distance from the impeller axis.

In some embodiments, the cannula may include a spiral support member, the spiral support member spiraling about the impeller axis. The spiral support member may be adjustable from the operable configuration to the deployment configuration by twisting the spiral support member. Alternatively or additionally, the spiral support member may be adjustable from the operable configuration to the deployment configuration by axially positioning a proximal and distal end of the spiral support member further away from one another. The cannula may further include a cover supported by the spiral support member.

The cover, in some instances, may comprise a plurality of inlet openings and/or an outlet opening permitting flow to exit the pump substantially perpendicularly to the impeller axis. In some embodiments, the cannula may also include a second section adjustable between an operable configuration having a second diameter and a deployment configuration having a diameter substantially smaller than the second diameter. In particular embodiments, the cannula can include a port fixation neck between the first and second cannula sections.

In further embodiments, the cannula may have an expandable member at one end, or it may have an expandable member at both ends. The expandable member is configured to increase in size, so that it can engage with an anatomical structure. In some embodiments, the expandable member is configured to engage with blood vessels. For example, the expandable member may be configured to engage with blood vessels such as the aorta, vena cavea, the superior vena cava, the inferior vena cava, other vessels, or combinations of these. In other embodiments, the expandable member may engage with other or additional structures in the body, or in the heart, such as one or more valves in the heart. The expandable member may engage with the tissue structure in such a manner as to reduce, substantially reduce, substantially prevent, or prevent blood flow between, by, or around the expandable member and the tissue structure with which the expandable member is engaged.

In some embodiments, the expandable member is configured to be positioned between a deployment configuration, which is generally collapsed for reduced or minimal size, and an operable configuration, in which the expandable member is partially or wholly expanded in size. In some embodiments, the expandable member may be expanded by being inflated with a fluid, such as air, saline, other physiological compatible fluid, or combinations of these. In other embodiments, the expandable member may be maintained in a constrained configuration when in the deployment configuration, such as by being restrained by a restraining member, such as a sheath. When the sheath or other restraining member is disengaged from the expandable member, the expandable member expands to a size that is greater than the size of the expandable member when in its deployment configuration. In still other embodiments, the expandable member may be maintained mechanically in a deployment configuration, such as by gears that engage with slots in the expandable member, where the gears are driven by a drive mechanism. In such embodiments, the drive mechanism can be used to expand or contract the expandable member by any desired extent.

In further embodiments, the impeller may have two or more rigid or semi-rigid masts or flexible support members supporting the flexible web, the support members in the operable configuration being substantially perpendicular to the impeller axis and in the deployment configuration being substantially parallel to the impeller axis. A distal catheter section may support a first one of the support members and a proximal catheter section may support a second one of the support members, at least one of the distal and proximal catheter sections being rotatable with respect to the other so as to radially offset the support members.

In other embodiments, a first end of the rigid or semi-rigid mast or flexible support member may be operably connected with a first catheter section of the impeller and a second end of the rigid or semi-rigid flexible support member may be operably connected with a second catheter section, at least one of the first and second catheter sections being axially positionable with respect to the other, such that as the catheter sections are positioned toward each other, the support member is forced toward the operable configuration and as the catheter sections are moved away from each other, the support member is forced toward the deployment configuration. Additionally, at least one of the first and second catheter sections may be rotatable with respect to the other so as to radially offset the first and second ends of the support members.

The pump may include a drive shaft for driving a rotating motion of the impeller. The drive shaft may include a proximal section having a first gear at its distal end and a distal section having a second gear at its proximal end, rotation of the proximal section being transferred to the distal section by adjacently positioning the first and second gears. In another embodiment, a power transmission system of the pump for driving a rotational motion of the impeller may include a mechanical generator for transferring fluid motion therethrough into rotational motion of the generator about the impeller axis and a first lumen driving fluid to the mechanical generator and a second lumen transferring fluid away from the mechanical generator. The mechanical generator may be operably connected with the impeller, thereby transferring rotational motion of the generator about the impeller axis to rotational motion of the impeller about the impeller axis.

In a further embodiment, the power transmission system may further include one or more first magnets radially positioned about the impeller axis and operably connected at or near a mechanical generator and rotatable thereby about the impeller axis and a magnet housing operably connected with the impeller and positioned adjacent the mechanical generator, the housing having one or more second magnets positioned about the impeller axis interacting with the first magnets to magnetically to cause rotational motion of the second magnets about the impeller axis.

The present disclosure, in yet a further embodiment, relates to a method of deploying a pump for cardiac support. The method may generally include providing a pump, such as that described above, inserting a catheter with the pump operably connected at or near the distal end thereof into a blood vessel with the cannula and impeller in their deployment configurations, guiding the pump to a desired location, and adjusting the cannula and impeller from their deployment configurations to their operable configurations.

Methods may also include adjusting the rigid or semi-rigid mast or flexible support member and flexible web to create a desired impeller blade angle. The impeller may be driven at a desired speed via a power transmission system. Additional methods may include adjusting the cannula and impeller back to their deployment configurations and removing the catheter and pump from the blood vessel.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

Figure 2:
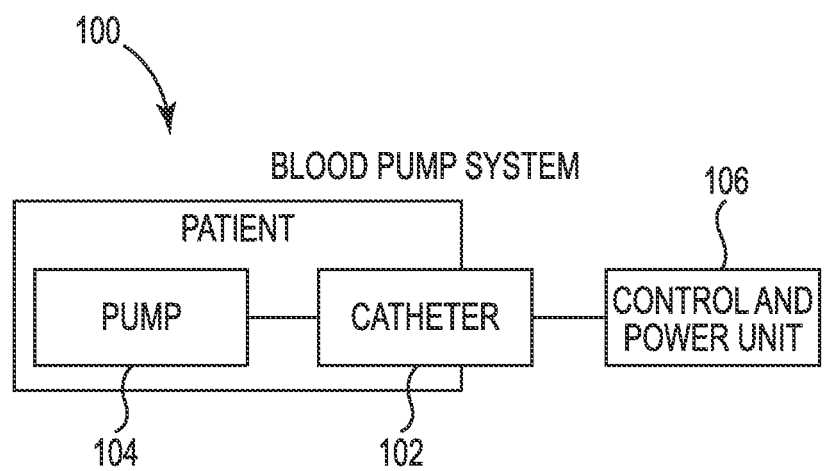
FIG. 2 is a schematic diagram of an expandable blood pump according to one embodiment of the present disclosure.

FIG. 1 illustrates one embodiment of an expandable blood pump 100 according to the present disclosure. With additional reference to FIG. 2, an expandable blood pump 100 may generally include a catheter 102 with a pump 104 positioned at or near the inserted end of the catheter and a control and/or drive unit 106 operably connected at or to an external end of the catheter. The pump 104 may include an impeller 108, a cannula 110, and a guidance system 112.

The catheter 102 may include a power transmission system operably coupling the pump 104 and the control and/or drive unit 106. Several of these components, such as but not limited to, the impeller 108, cannula 110, guidance system 112, and power transmission system, can have various embodiments, which may be interchanged or interchangeable within the blood pump 100 to create a variety of different blood pump embodiments, which will be understood from the following description.

Impeller

In general, the various embodiments of impellers of the present disclosure may include one or more impeller blades comprising a thin, flexible web or film of material. In some embodiments, the blades are suspended by or between one or more generally moveable, flexible, rigid or semi-rigid support members or masts. In other embodiments, the blades are made up of a material that does not use a support member or mast, such as where the blade is a collapsible, foldable, expandable, or inflatable section of polymer, web, Nitinol or another memory metal, or another biologically suitable material, or a composite or combination of these. In some embodiments of impellers disclosed herein, the impeller may be activated between a collapsed, deployment configuration and an expanded, operable configuration by changing the position of the moveable, rigid or semi-rigid support members, thereby stretching the flexible web into a desired position and creating an impeller blade surface. In other embodiments of impellers disclosed herein, the impeller may be activated between a collapsed, deployment configuration and an expanded, operable configuration by changing the position of the blades, by inflating the impeller, or by restraining the blades or allowing them to unfold or expand into their operable configuration of increased or maximum size. Thus, the impeller may permit a collapsed, deployment configuration of reduced or minimum size and an expanded, operable configuration of increased or maximum size.

In some embodiments, the impeller may be activated between a collapsed, deployment configuration and an expanded, operable configuration separately from an activation of the cannula (discussed in further detail below) between a collapsed, deployment configuration and an expanded, operable configuration. Alternately, expansion of cannula and impeller may occur together, at substantially the same time. In various embodiments disclosed herein, the impeller blades' geometries and scales can reduce hemolysis, thereby improving procedure outcomes due to improved therapy. Further, the impeller may be located within the cannula at any axial distance from the distal tip.

Figure 3:
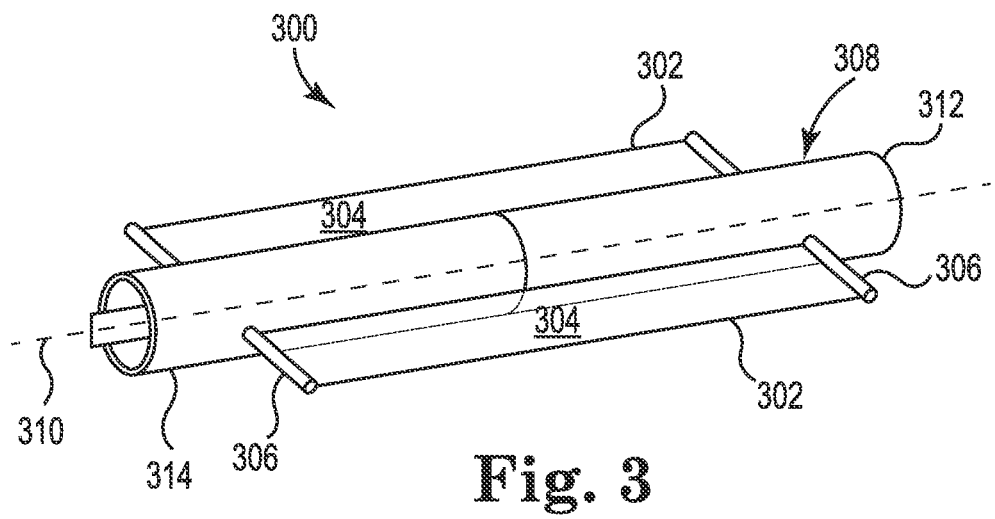
FIG. 3 is a perspective view of an impeller according to one embodiment of the present disclosure.

In one embodiment, illustrated in FIG. 3, an impeller 300 may be comprised of one or more impeller blades 302, each blade having a flexible web 304 suspended between rigid or semi-rigid, cantilevered support members 306 attached to the catheter 308. The support members 306 may be rotated or adjusted between positions substantially parallel and perpendicular to the pump's rotational axis 310. With the support members 306 in a position substantially parallel to the pump's rotational axis 310, the flexible web 304 may be retracted therewith to a collapsed, deployment configuration. As the support members 306 are adjusted to a position substantially perpendicular to the pump's rotational axis 310, as illustrated in FIG. 3, the flexible web 304 may be extended therewith to an expanded, operable configuration.

The catheter 308 may include a catheter layer having a proximal section 312 and a distal section 314, which may be rotated relative one another. Each blade 302 may have a support member 306 positioned at the proximal section 312 and a support member at the distal section 314. In this manner, with the flexible web 304 in an expanded, operable configuration, the angle of the flexible web, and thus the impeller blade surface, may be created or modified by rotation of the proximal 312 and distal 314 sections of the catheter 308 relative one another.

Figures 4A, 4B:
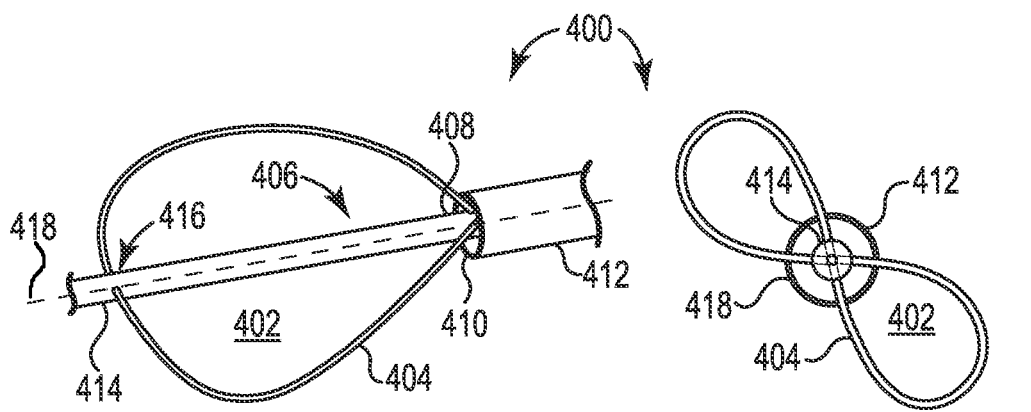
FIG. 4A is a perspective view of an impeller according to another embodiment of the present disclosure.
FIG. 4B is an end view of the impeller of FIG. 4A.

In another embodiment, illustrated in FIGS. 4A and 4B, an impeller 400 may include a flexible web 402 suspended by or between a generally semi-rigid, but flexible support member 404 and optionally the catheter 406. The generally semi-rigid, but flexible support member 404, in some embodiments, may be but is not limited to a moderate stiffness wire, and may be attached at both ends 408, 410 to the catheter 406. In one embodiment, the catheter 406 may include a sliding section 412 and a rotational section 414, which may be rotated relative to the sliding section, and the support member 404 may be attached at both ends 408, 410 to the sliding section of the catheter. A portion of the support member 404 may also be generally held in place axially at a fixed location 416 along the rotational section 414.

For example, in one embodiment, the flexible support member 404 may pass through the rotational section 414, as shown in FIG. 4A, such that a portion of the support member is generally held in place axially at fixed location 416 along the rotational section. In another embodiment, the support member 404 may be split into two sections, each section having an end attached to the sliding section 412 and an end attached to the rotational section 414 at fixed location 416. However, other suitable elements for permitting proximal and distal ends of the flexible support member 404 to move axially relative one another are considered within the spirit and scope of the present disclosure. Where a support wire is used for one or more flexible supports, the support wire may be round or flat. Alternatively, the supports may be formed from a cut tube, hollow wire, or similar structure.

The sliding section 412 of the catheter 406 may be slid or axially adjusted along the rotational section 414 between axial positions toward and away from fixed location 416. With the sliding section 412 slid to a position generally relatively away from fixed location 416, portions of the support member 404 may be pulled closer to the pump's rotational axis 418, thereby causing the flexible web 402 to be retracted therewith to a collapsed, deployment configuration.

As the sliding section 412 is slid to a position generally relatively toward the fixed location 416, portions of the support member 404 may be forced away from the pump's rotational axis 418, thereby causing the flexible web 402 to be expanded therewith to an expanded, operable configuration, as illustrated in FIG. 4A. With the flexible web 402 in an expanded, operable configuration, the angle of the flexible web, and thus the impeller blade surface, may be created or modified by rotation of the rotational section 414 of the catheter 406 with respect to the sliding section 412, as illustrated in FIG. 4B.

Figures 5A, 5B:
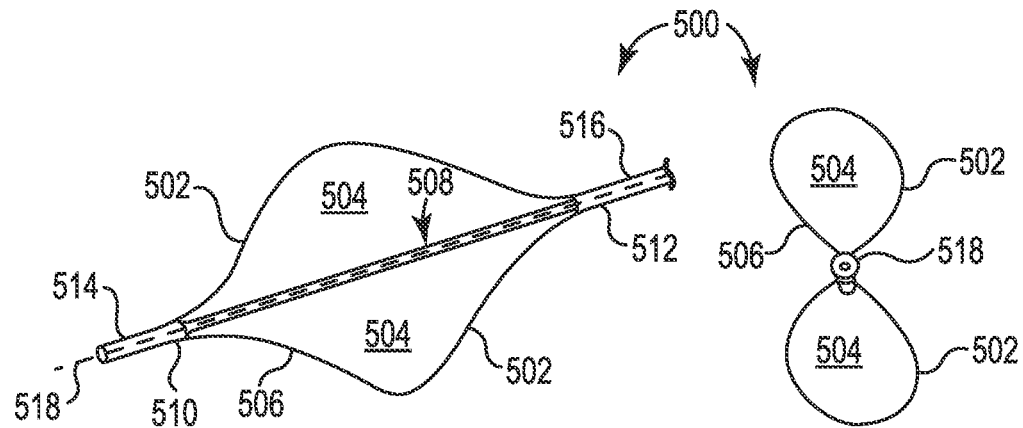
FIG. 5A is a perspective view of an impeller according to yet another embodiment of the present disclosure.
FIG. 5B is an end view of the impeller of FIG. 5A.

In yet another embodiment, illustrated in FIGS. 5A and 5B, an impeller 500 may include one or more impeller blades 502, which may each include a flexible web 504 suspended by or between a generally semi-rigid, but flexible support member 506 and optionally the catheter 508. The generally semi-rigid, but flexible support member 504, in some embodiments, may be but is not limited to a moderate stiffness wire, and may be attached at both ends 510, 512 to the catheter 508.

In one embodiment, the catheter 508 may include a catheter layer having a proximal (alternatively, distal) section 514 and a distal (alternatively, proximal) section 516, with either or both sections axially positionable along the pump's rotational axis 518 and either or both sections rotatable about the pump's rotational axis, such that the distal and proximal sections may be axially positioned and rotated relative to one another.

The support member 506 may be attached at one end 510 to the distal section 514 and at one end 512 to the proximal section 516, thereby permitting the ends to also be axially positioned and rotated relative one another by means of the distal and proximal sections. However, other suitable elements for permitting distal 510 and proximal 512 ends of the flexible support member 506 to move axially and/or rotationally relative one another are considered within the spirit and scope of the present disclosure.

Figure 5C:
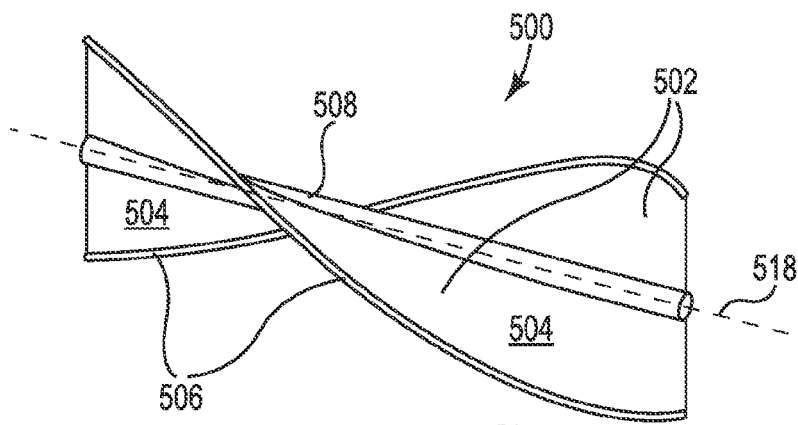
FIG. 5C is a perspective view of the impeller.
Figure 5D:
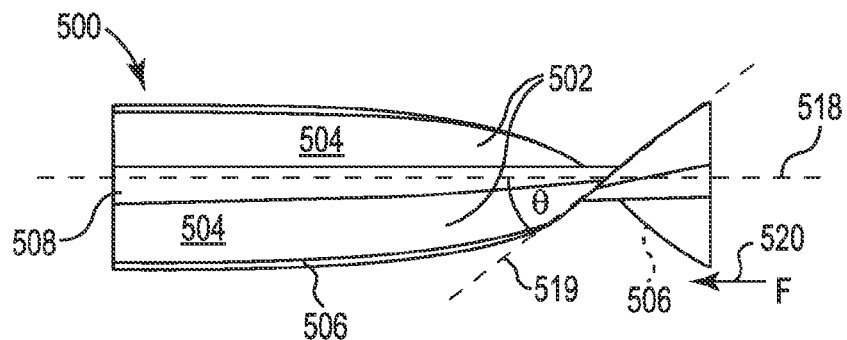
FIG. 5D is a side view of the impeller, showing a possible flow direction.
Figure 5E:
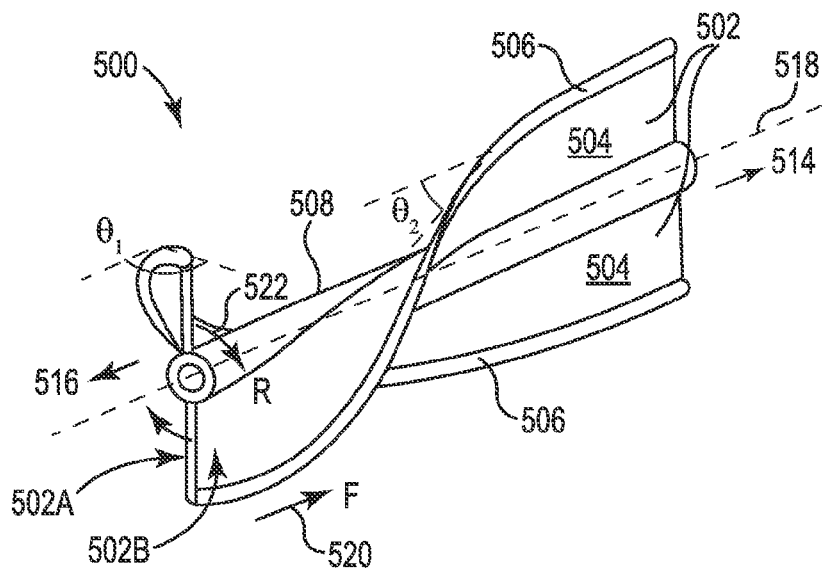
FIG. 5E is an alternate perspective view of the impeller, showing a possible rotational direction.

As shown in FIGS. 5C, 5D, and 5E, the impeller geometry may be characterized by a blade angle ($\theta_1$) at the inlet that will be sharper (more perpendicular and less parallel to the axis of rotation) and a blade angle ($\theta_2$) at the outlet that will be flatter (more parallel to the axis of rotation). The transition between the two angles may occur gradually, in order to improve flow performance and reduce turbulence and other losses.

For example, the blade angle ($\theta$) may be measured between the direction of axis (or rotational axis) 518 and a tangent line 519 to the impeller blade 502, as shown in FIG. 5B, where the tangent line 519 is defined at the radially outer portion of the web 504, or along flexible support 506. Further, the inlet or proximal blade angle ($\theta_1$) may be relatively larger toward the proximal or inlet section 516 of impeller 500; that is, with the blade edge or tangent line along flexible support 506 or the outer portion of web 504 oriented more or less perpendicularly to the direction of axis 518. Conversely, the outlet or distal blade angle ($\theta_2$) may be relatively smaller ($\theta_2 < \theta_1$) toward distal or outlet section 514; that is, with the blade edge or tangent along flexible support 506 or the outer portion of web 504 oriented more or less parallel to or along the direction of axis 518.

Where the blade transition angle changes gradually, the value of the blade angle ($\theta$) may be substantially continuous, with a substantially continuous (e.g., first) derivative between distal end 514 and proximal end 516 of axial member or catheter 508. Further, the blade angle may vary from approximately perpendicular or somewhat less than perpendicular toward the proximal end 516 (that is, $\theta_1 \leq 90°$), to approximately parallel or somewhat greater than parallel toward the distal end 514 ($\theta_2 \geq 0°$). Alternatively, the blade angle ($\theta$) may vary between upper and lower bounds, or both, for example $\theta \geq 10°$, $\theta \geq 20°$, or $\theta \geq 30°$; and/or $\theta \leq 80°$, $\theta \leq 70°$, or $\theta \leq 60°$.

The relationship between the proximal 516 and distal 514 sections of catheter 508 may also be reversed, so that $\theta_1 > \theta_2$. Similarly, in some embodiments the direction of flow F (arrow 520) may proceed in either direction along impeller 500, from end 514 toward end 516 or from end 516 toward end 514, without loss of generality.

In further embodiments, the blade angle ($\theta$) may be substantially constant along impeller 500, such that $\theta_1 \approx \theta_2$, or the blade angle ($\theta$) may increase or decrease substantially monotonically between $\theta_1$ and $\theta_2$, where $\theta_1 \neq \theta_2$. Where the blade angle varies, the variation may be linear as a function of axial position z. For example, the blade angle may be defined as:

$$\theta(z) = \theta_1 + mz, \tag{1}$$

where the slope is $m = (\theta_1 - \theta_2)/\Delta z$, and $\Delta z = z_2 - z_1$, the axial spacing between the first and second blade angles $\theta_1$ and $\theta_2$, respectively.

In a logarithmic profile, the blade angle may vary as:

$$\theta(z) = \theta_1 + \Delta\theta \times \log[1 + (b-1)(z-z_1)/\Delta z], \tag{2}$$

where $\Delta\theta=\theta_2-\theta_1$ and b is the base of the logarithm, such that $\theta(z_1)=\theta_1+\theta_2\times\log(1)$, which is $\theta_1$, and such that $\theta(z_2)=\theta_1+\Delta\theta\times\log(b)$, which is $\theta_2$. Alternatively, the variation may be sinusoidal:

$$\theta(z)=\theta_1+\Delta\theta\times\sin[(z-z_1)\pi/n\Delta z], \quad [3]$$

where n determines the periodicity, for example n=2. The blade angle (θ) may also vary exponentially, or take another functional form. The blade angle (θ) may also have local minima and maxima between $\theta_1$ and $\theta_2$.

Either or both of the distal 514 and/or proximal 516 sections of the catheter 508 may be slid or axially adjusted along the pump's rotational axis 518 between axial positions toward and away from the other. With the distal 514 and proximal 516 sections adjusted to a position generally relatively away from each other, portions of the support member 506 may be pulled closer to the pump's rotational axis 518, thereby causing the flexible web 504 to be retracted therewith to a collapsed, deployment configuration.

As the distal 514 and proximal 516 sections are adjusted to a position generally relatively toward each other, portions of the support member 506 may be forced away from the pump's rotational axis 518, thereby causing the flexible web 504 to be expanded therewith to an expanded, operable configuration, as illustrated in FIG. 5A. With the flexible web 504 in an expanded, operable configuration, the angle of the flexible web, and thus the impeller blade surface, may be created or modified by rotation of either or both of the distal 514 and/or proximal 516 sections of the catheter 410 with respect to one another, as illustrated in FIG. 5B.

Rotation of the impeller 500 in or along an operational direction R (arrow 522) may be a mechanism for impeller 500 to deploy and expand, utilizing fluid flow, pressure, bias, centrifugal force, or a combination thereof to spread webs 504 in a radially outward position with respect to rotational axis 518; that is, with blades 502 in an operable position outward of catheter 508. Rotation in the opposite direction may cause the mechanism to collapse, with blades 502 positioned closer to catheter 508, and webs 504 gathered into a more radially inward position with respect to axis 518.

Generally, the operational direction of rotation R may be from a relatively higher pressure surface of blade (or blade pair) 522 toward a relatively lower pressure surface of blade (or blade pair) 502, as shown in FIG. 5E. In some embodiments, web 504 also flexes under load to generate a substantially concave pressure surface along one side of blade 502 (e.g., 502A) and a substantially convex suction surface along the opposite side or blade 502 (e.g., 502B). Alternatively, the operational direction or curvature (or both) may be reversed, based on flow conditions and the power or torque supplied to impeller 500.

The various embodiments of cannulas described above may be manufactured from any suitable materials. For example, the various embodiments of cannulas described above may be manufactured from, but are not limited by, a polymer, a flexible web, a metal or metal alloy, a shape memory material, or combinations of materials. The material of webs 504 may also be a woven mesh attached to the support members 506, such as a Nitinol or fabric weave. The mesh may be left with openings for improved flow dynamics, and the mesh may be coated. Where a coating is used, the coating may be silicone or polyurethane (PU).

The support members or masts 506 may further be formed of or comprise straight or curved wire, braided wire or tubing, for example laser cut tubes or laser cut tubing. One or both of web 504 and support members 506 may also be formed of or include an additional cover material, for example (expanded) polytetrafluoroethylene (ePTFE or PTFE), high density polyethylene (HDPE or PEHD), polyethylene terephthalate (PET or PETE), or a polyimide or silicone material. Where laser cutting or cut tubing is described, laser cutting and other forms of pattern cutting may be employed, for example by cutting a formed tube or sheet of material such as Nitinol or another memory metal, or another biologically suitable metal alloy, polymer or composite material.

Cannula

In general, the various embodiments of cannulas of the present disclosure may include a plurality of support members or ribs, and may be activated between a collapsed, deployment configuration and an expanded, operable configuration by changing the relative position of the ribs. In some embodiments, as noted above, the cannula may be activated between a collapsed, deployment configuration and an expanded, operable configuration separately from an activation of the impeller between a collapsed, deployment configuration and an expanded, operable configuration.

In an expanded, operable configuration, a conduit may be created within which the pump's impeller may be expanded and operated. Operation of the impeller can generate blood flow within the cannula between the cannula's inlet and outlet, which may typically be provided at the proximal and distal ends, respectively, of the cannula. In some embodiments, the cannula may also provide separation between any surrounding tissue and the impeller.

Figure 6:
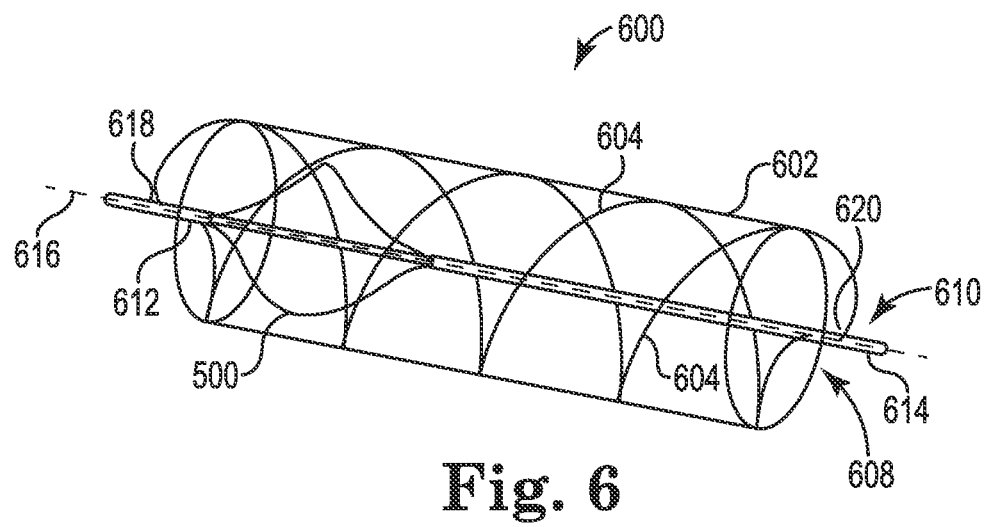
FIG. 6 is a perspective view of a cannula according to one embodiment of the present disclosure.
Figure 7C:
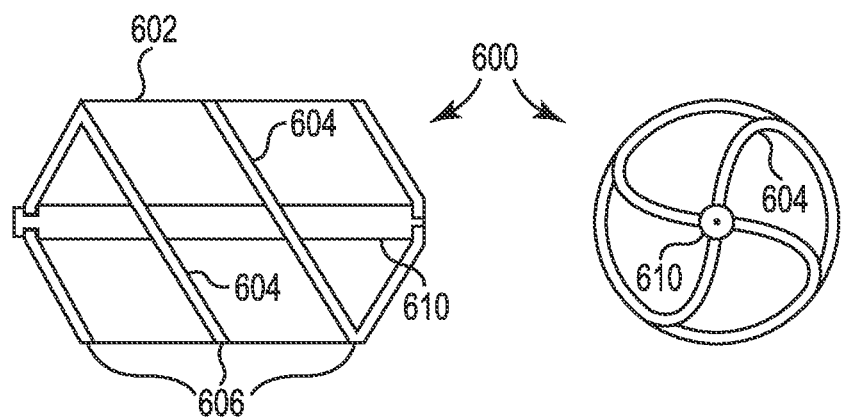
FIG. 7C is a side schematic view of the cannula embodiment of FIG. 6 in a collapsed configuration.
Figure 7C:

In one embodiment, illustrated in FIG. 6 and schematically in FIGS. 7A, 7B, and 7C, a cannula 600 may include a thin, flexible film or mesh cover 602 supported by or between one or more substantially rigid or semi-rigid support members 604 in spiral configuration, creating a plurality of ribs 606. In an expanded, operable configuration, as illustrated in FIG. 6, the ribs 606 may stretch and/or support the cover 602 to create a conduit 608, in which the impeller (e.g., impeller 500 as shown in FIG. 6; although any of the above described impellers are suitable) may by expanded to its operable configuration. In some embodiments, the substantially rigid or semi-rigid support members 604 in spiral configuration may be biased to the expanded, operable configuration.

The cannula 600 may be adjusted from an open or operational configuration, as shown in FIGS. 7A and 7B, to a collapsed, deployment or insertion configuration, as illustrated in FIG. 7C. In one embodiment, with reference again to FIG. 6, the catheter 610 may include a catheter layer having a distal section 612 and a proximal section 614, with either or both sections axially positionable along the pump's rotational axis 616, such that the distal and proximal sections may be axially positioned relative to one another.

The cannula 600, or more particularly in some embodiments, the support members 604, may be attached at one end 618 to the distal section 612 and at one end 620 to the proximal section 614, thereby permitting the ends of the cannula 600, or support members 604, to also be axially positioned relative one another by means of the distal and proximal sections. Thus, in one embodiment, the cannula 600 may be adjusted from an open configuration to a collapsed, deployment configuration by causing the support members 604 to be adjusted axially generally relatively away from each other, thereby causing portions of the support members to be pulled closer to the pump's rotational axis 616, and causing the flexible mesh cover 602 to be retracted therewith.

In addition or alternatively, either or both of the distal 612 and proximal 614 sections may be rotatable about the pump's rotational axis 616, such that the distal and proximal sections may be rotated relative to one another. In this regard, the ends of the cannula 600, or support members 604, may additionally or alternatively be rotatably positioned relative one another by means of the distal 612 and proximal 614 sections. Thus, in one embodiment, the cannula 600 may be adjusted to a collapsed, deployment configuration by additionally or alternatively causing the ends of the spiral support members 604 to be rotated relative one another other, thereby shrinking the size of the conduit 608 and collapsing the mesh cover 602 supported there between.

However, any other suitable elements for permitting distal 618 and proximal 620 ends of the support members 604 to move axially and/or rotatably relative one another are considered within the spirit and scope of the present disclosure. In a further embodiment, cannula 600 and/or catheter 610 may include a drawstring, which may be pulled to gather up any loose material of the retracted mesh cover 602 and hold the mesh cover relatively closer to the catheter body.

Figure 7D:
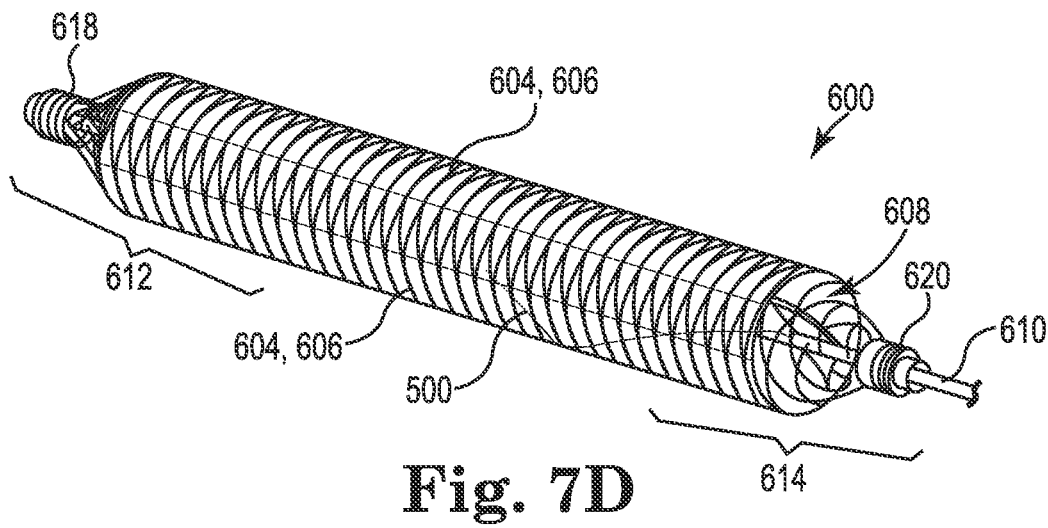
FIG. 7D is a perspective view of a cannula embodiment with support members formed of a wire braid.
Figure 7E:
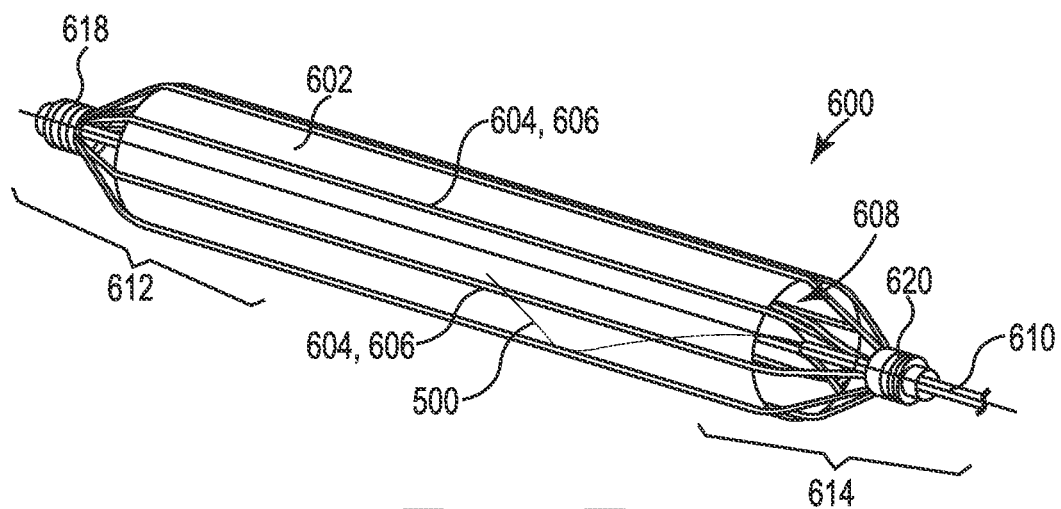
FIG. 7E is a perspective view of a cannula embodiment with support members forming a tubular frame.

The support members 604 and ribs 606, or both, may be formed from a wire frame or braid or a laser-cut shape memory tube, as shown in FIGS. 7D and 7E. There may also be a combination design of straight, substantially longitudinal or axial support members 604 or ribs 606 supported at the proximal 614 and distal 612 ends of the cannula 600, and a braided or mesh pattern of substantially circumferential or helical support members 604 or ribs 606 in the center, between ends 614 and 612.

The pattern may also be reversed, with a circumferential or helical braided or mesh pattern of support members 604 or ribs 606 on the ends, and a substantial straight and axial or longitudinal pattern of support members 604 or ribs 606 in between. Where the rib pattern 606 is formed from a laser cut tube support member 604, the geometry may also be provided without or substantially without projections, for example without sharp projections that could snag on a sheath or similar element that may be provided over the cannula 600, or which could ride over the cannula 600 in the collapsed or deployment configuration.

Figure 7F:
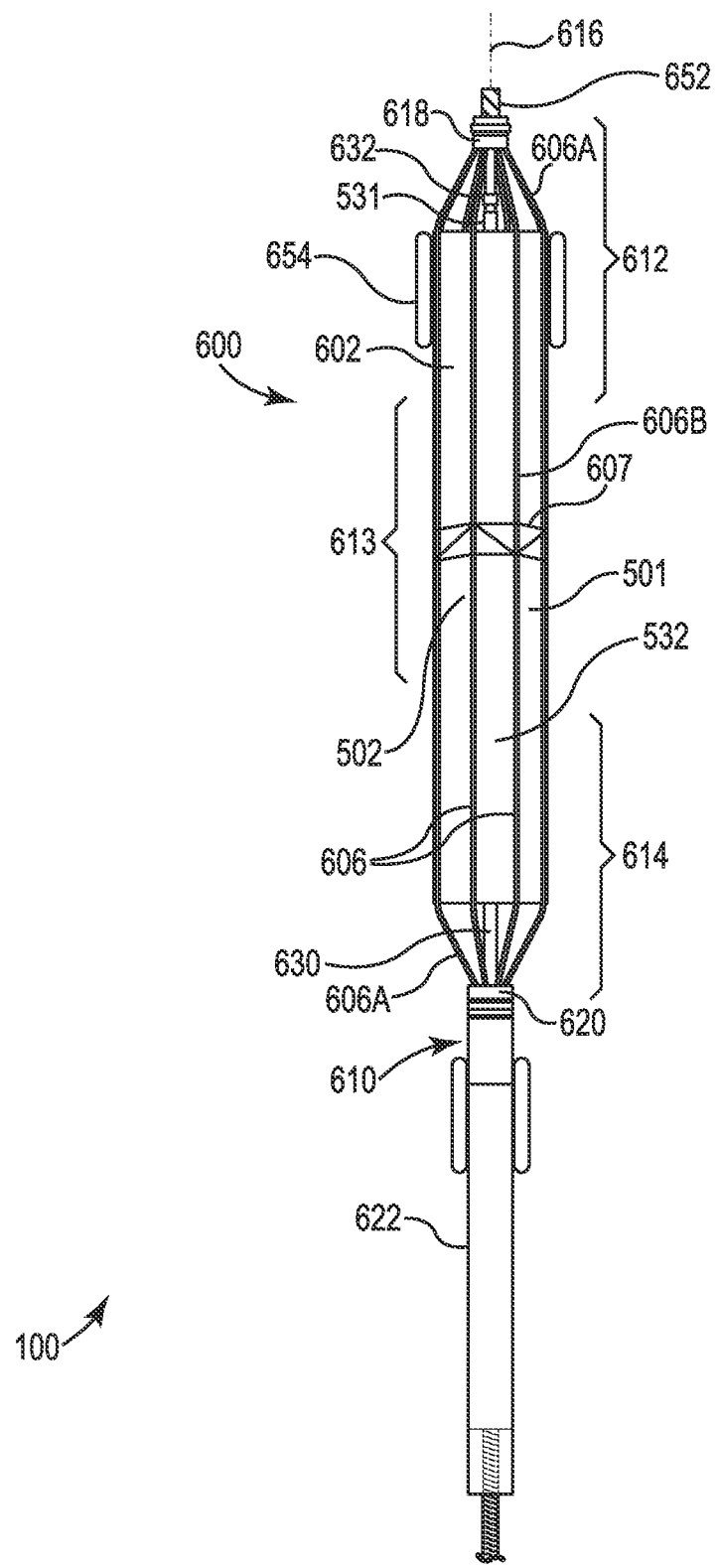
FIG. 7F is a side view of the tubular frame cannula embodiment.

FIG. 7F is a side view of cannula 600 in a tubular frame embodiment. In this configuration, cannula 600 includes a support structure, formed of substantially straight and axially aligned ribs 606 extending from proximal end or region 614 to distal end or region 612, with at least one cross-bracing structure 607 in intermediate or middle region 613, between ends 612 and 614.

The support structures 606 and 607 of cannula 600 may for formed, for example, by laser cutting from a memory metal such as a Nitinol tube, or using another suitable material as described herein. For example, the configuration of FIG. 7F may be formed similarly to the embodiment of FIG. 7E, with cross-brace structure 607 formed in a sinusoidal, sawtooth or stent-like pattern for added circumferential strength in mid region 613. Alternatively, cross-brace 607 may be formed of one or more helical or circumferential ribs, as described above.

Support ribs 606 are fixed or attached to catheter 610 at one end, for example first end 620 of proximal region 614. The opposing end (e.g., second end 618 of distal region 612) floats in the axial dimension with respect to catheter 610 and proximal end 620. As sheath 622 is slid off of the collapsed cannula 600, support members 606 and 607 may be biased to expand into their operational form, with longitudinal ribs 606 extending radially and axially from first end 620 into proximal region 614, substantially axially from proximal region 614 through mid region 613 and into distal region 612, and axially and radially from distal region 612 to second end 618. Cross brace structure 607 expands substantially circumferentially and radially to support mid region 613 of cannula 600, as described above.

Mesh cover 602 may be formed of ePTFE or polyurethane, as described above, or of another suitable fabric material, or of silicone. As cannula sheath 622 is retracted to deploy cannula 622 by sliding in the proximal direction, second (free end) 618 will typically slide or reposition toward first (fixed) end 610, opening cannula 600 and mesh 602 up in the radial direction for deployment and operation. Support members 606 and 607 deform from the deployment state into the operational state, expanding mesh or cover 602 to form a flow passage for impeller 500. As sheath 622 slides back in a distal direction, support members 606 and 607 and mesh 602 are covered by sheath 622, deforming back from the operational state into the deployment state for removal.

Impeller 500 may be formed with blades formed of a memory metal such as Nitinol, or they may be a memory metal such as Nitinol wires 501 covered with a mesh or web material to form blades 502, as described above, with blades 502 and wires 501 fixed to drive shaft 630 on proximal end 532 of blades 502 and impeller 500. Distal end 531 of impeller 500 and blades 502 floats in the axial dimension with respect to proximal end 532.

As cannula 600 expands, support members 607 and 606 are biased into their operational form and distal (free) end 531 of impeller 500 slides or displaces axially toward the proximal (fixed) end 532. Stop 632 may be provided on drive shaft 630 in distal region 612 to prevent over-travel of free impeller end 531, for example between free end 531 and distal end 618 of cannula 606. Suitable cover materials for impeller 500 and blades 502 (e.g., web 504, above), and for cannula 600 (e.g., cover material 602) include silicone, polyurethane, biologically suitable fabric materials, wire mesh, and cut metal sheet, and combinations thereof, for example with one material selected for use as a structural form and another selected for use as coating or web.

Drive shaft 630 may be formed of a flexible wire coil in at least a portion of proximal region 614, for example until drive shaft 630 reaches impeller 500 at proximal end 532. Drive shaft 630 may be formed of a substantially straight or semi-rigid wire in mid region 613 and distal region 612, for example from proximal end 532 through distal end 531, stop 632 and distal end 618 of cannula 600. In proximal region 614, drive shaft 630 is supported by catheter 610 at end 620. In distal region 612, drive shaft 630 may be supported by a short section of catheter at distal end 618 of cannula 600, where distal end 618 is supported by structural members 606 and 607.

In contrast to other designs, longitudinal supports 606 include radially and axially extending portions 606A in proximal and distal regions 614 and 612, and substantially axially extending regions 606B in mid section 613, between proximal and distal regions 614 and 612. Further, drive shaft 632 may extend from first (proximal) end 620 of cannula 600 at catheter 610 through proximal region 614, mid region 613 with impeller 500, and distal region 612 with stop 632 to second (distal) end 618. Thus, cannula 600 is axially and radially fixed to catheter 610 at proximal end 620 via radial and axial load supporting portions 606A of supports 606, in proximal region 614.

In distal region 612, however, while axial/radial portions 606A of longitudinal supports 606 fix distal end 618 of cannula 600 in a radial sense about drive shaft 630, distal end 618 may slide along drive shaft 630 to provide freedom of motion in the axial direction with respect to proximal end 620, as described above. Alternatively, distal end 618 of cannula 600 may be radially fixed with respect to drive shaft 630, with axial freedom of motion provided by sliding drive shaft axially within catheter 610.

This avoids the axially folded deployment configurations of some fixed-fixed designs, while providing radial support to fix distal end 618 of cannula 600 in a radial sense, avoiding structural issues raised by fixed-free designs. In this axially floating configuration of cannula 600 at distal end 618, sheath 622 is configured to push over and back over the full axial length of cannula 600, in both proximal (opening) and distal (collapsing) direction, without binding.

Alternatively, proximal end 620 of cannula 600 may be configured to slide axially with respect to catheter 610 and (fixed) distal end 618, so that cannula 600 may be deployed or collapsed by distal and proximal axial motion of drive shaft 630 with respect to catheter 610 and (e.g., axially stationary) sheath 622, where drive shaft 630 is axially fixed to cannula 630 at distal end 618, as described above. In this configuration, axial motion of drive shaft 630 could also be utilized to collapse and deploy impeller 500, in combination with cannula 600, where impeller 500 would collapse and deploy within cannula 600, and cannula 600 would collapse and deploy as proximal end 620 is drawn into or extended out from (e.g., axially stationary) sheath 622.

One or both of cannula 600 and catheter 610 may also be provided with fixing elements to position or retain pumping system 100 with respect to an anatomical element, for example a vascular wall, valve, or anatomical feature of the heart. In various embodiments, for example, a screw or other mechanical retainer or coupling element 652 may be provided at the tip of pump system 100, for example on the catheter section of distal end or tip 618 of cannula 600, in order to secure cannula 600 and pump system 100 to a cardiac wall.

Alternatively, one or more hook or tine-type mechanical retainers 652 may be provided, for example as configured to deploy in combination with cannula 600, in order to attached to a trebecula or similar trabeculation formation within a chamber of the heart, or a similar feature on the cardiac wall. One or more retainers 652 may also be provided as a guidewire anchor to attach or anchor the guidewire, as described below, where pump system 100 is positioned by running out over the guidewire and into a desired anchor location.

In further embodiments, one or more balloons or other expansion elements 654 may be provided outside of cannula 600, in order to secure pump 100 to a vascular feature such as a valve or aorta wall. Balloon elements 654 may expand by action of a biasing element, as described above, or through fluid pressurization, for example as provided by pump 100 or via an additional channel or lumen, for example as coupled to a fluid drive system, as described below.

Balloon elements 654 may be provided in any combination of proximal, mid and distal regions 614, 613 and 612 of cannula 600. Balloon elements 654 may also be provided along catheter 610 or sheath 622, in order to secure catheter 610 to an aorta wall or other vascular structure.

Figures 8A, 8B:
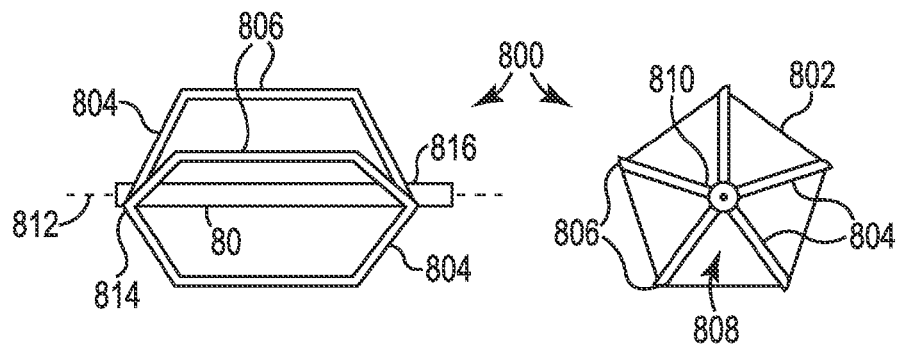
FIG. 8A is a side schematic views of a cannula embodiment in an expanded configuration.
FIG. 8B is an end schematic view of the cannula embodiment of FIG. 8A.
Figure 8C:
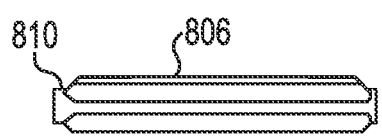
FIG. 8C is a side schematic view of the cannula embodiment of FIG. 8A in a collapsed configuration.

In another embodiment, illustrated schematically in FIGS. 8A, 8B, and 8C, a cannula 800 may include a thin, flexible film or mesh cover 802 supported by or between one or more substantially rigid or semi-rigid support members 804 in a linear, axial configuration, creating a plurality of ribs 806 that are generally aligned parallel to the catheter body. In an expanded, operable configuration, as shown in FIGS. 8A and 8B, the ribs 806 may stretch and/or support the cover 802 to create a conduit 808, in which the impeller may by expanded to its operable configuration. In some embodiments, the substantially rigid or semi-rigid support members 804 in a linear, axial configuration may be biased to the expanded, operable configuration.

Similar to the embodiments of FIGS. 6 and 7, the cannula 800 may be adjusted to a collapsed, deployment configuration, as illustrated in FIG. 8C. In one embodiment, as discussed above, the catheter 810 may include a catheter layer having a distal section and a proximal section, with either or both sections axially positionable along the pump's rotational axis 812, such that the distal and proximal sections may be axially positioned relative to one another. The cannula 800, or more particularly in some embodiments, the support members 804, may be attached at one end 814 to the distal section and at one end 816 to the proximal section, thereby permitting the ends of the cannula 800, or support members 804, to also be axially positioned relative one another by means of the distal and proximal sections.

Thus, in one embodiment, the cannula 800 may be adjusted to a collapsed, deployment configuration by causing the support members 804 to be adjusted axially generally relatively away from each other, thereby causing portions of the support members to be pulled closer to the pump's rotational axis 812, and causing the flexible mesh cover 802 to be retracted therewith. Conversely, the cannula 800 may be opened to an expanded or operable configuration by causing the support members 804 to be adjusted axially generally relatively toward one another, thereby causing portions of the support members to be positioned away from the pump's rotational axis 812, and causing the flexible mesh cover 802 to be expanded or deployed therewith. This may be accomplished, for example, by relative axial positioning of the proximal 816 and distal 814 ends of cannula 800, or the corresponding proximal and distal portions of catheter 810.

As with the above embodiments, any other suitable elements for permitting distal 814 and proximal 816 ends of the support members 804 to move axially relative one another are considered within the spirit and scope of the present disclosure. In a further embodiment, cannula 800 and/or catheter 810 may include a drawstring, which may be pulled to gather up any loose material of the retracted mesh cover 802 and hold the mesh cover relatively closer to the catheter body. In each of these embodiments, collapse of the cannula 800 may also cause the impeller to collapse to the deployment position, and expansion or deployment of the cannula 800 may also allow the impeller to expand from the collapsed deployment position and to open outward to an operable or deployed position.

In some embodiments, as illustrated in FIGS. 6-8C, the cannula may have a generally constant diameter axially along the catheter body. However, in other embodiments, as illustrated for example in FIG. 9A, the cannula 900 may have a diameter that varies axially along the catheter body 902. In such embodiments, the cannula 900 may have two or more axial sections 904, 906 of substantially constant diameters and one or more axial sections of transition 908 from one section of constant diameter to a different section of constant, but different, diameter.

Figure 9A:
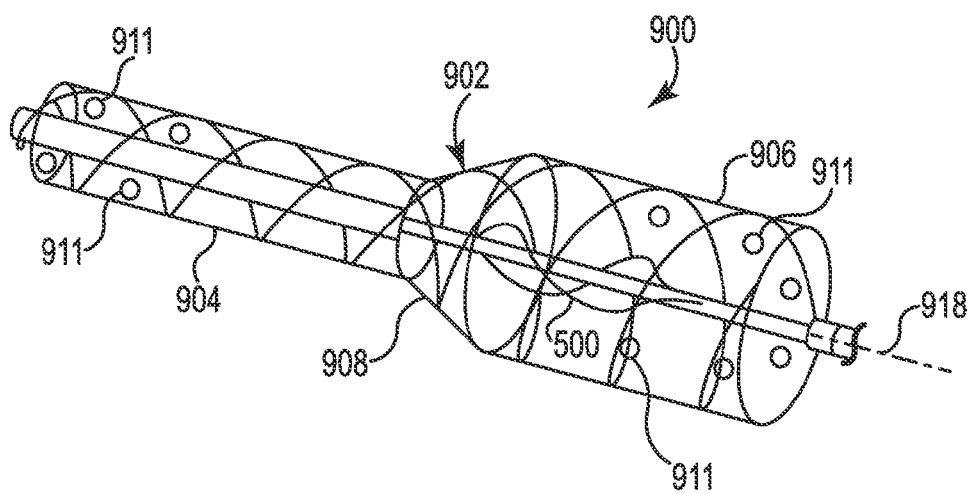
FIG. 9A is a perspective view of a cannula according to still a further embodiment of the present disclosure having various diameters along its axial length.

An impeller, such as those described above, may be provided in any suitable axial section. As illustrated, an impeller (e.g., impeller 500 as shown in FIG. 9A; although any of the above described impellers are suitable) may be provided within a proximal axial section 906 of relatively larger diameter than a distal axial section 904. In such an embodiment, the transition from a relatively larger diameter conduit to a relatively smaller diameter conduit may also increase the rate of flow through the distal axial section 904 and out of cannula 900.

According to some embodiments, operation of an impeller within the various embodiments of cannulas described herein may cause a flow of fluid, e.g., blood, into an inlet opening at one end of the cannula, through the cannula, and out an outlet opening at an opposite end of the cannula. Generally, the flow of fluid may be substantially axial with the axis of rotation of the impeller. However, in some embodiments, a cannula 900 may additionally or alternatively include inlet 911 or outlet openings 909 that permit the flow of fluid in or out of the cannula 900, substantially perpendicularly to the axis 918 of rotation of the impeller. In still other embodiments, a cannula may include multiple inlets 911, for example in the inlet section or proximal axial section 906 of cannula 900, and/or multiple outlets 909, for example in the outlet section or distal axial section 904 of cannula 900, which may assist in preventing blockages of the inflow and/or outflow of fluid to or from the pump.

Figure 9B:
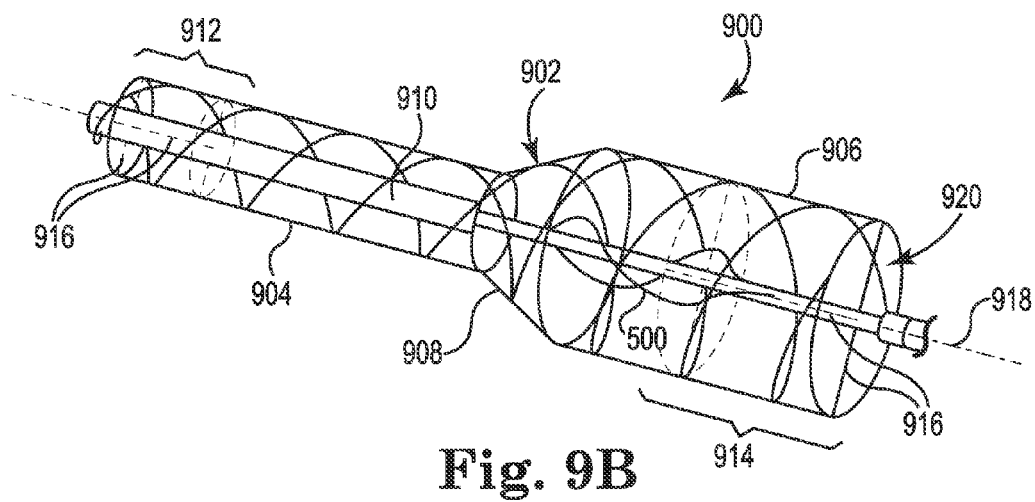
FIG. 9B is a perspective view of a cannula with radial flow straighteners.
Figure 9C:
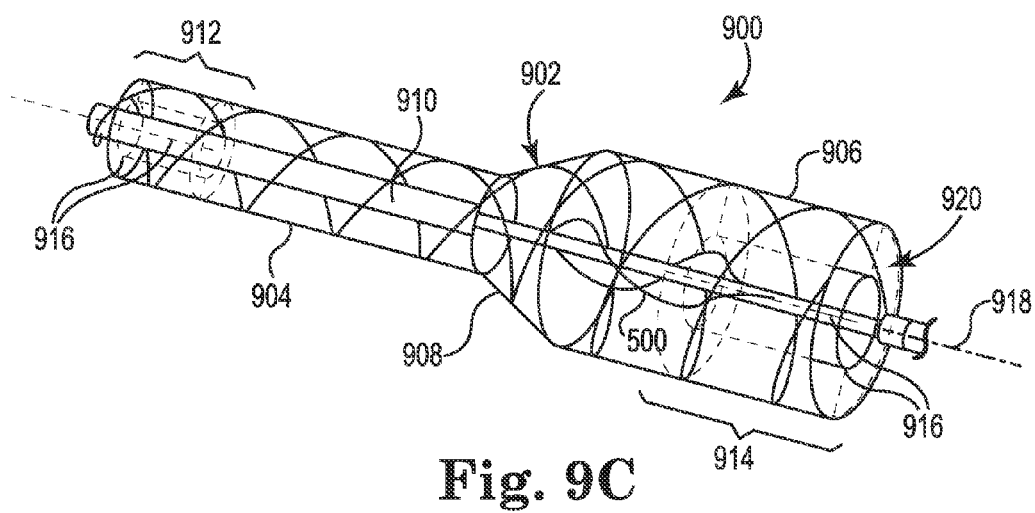
FIG. 9C is a perspective view of a cannula with concentric flow straighteners.

The cannula 900 and other devices described herein may also utilize flow straighteners, for example flow straighteners 916 as shown in FIGS. 9B and 9C. Flow straighteners 916 may be comprised of one of more flexible membranes that extend radially from the catheter 910 to the cannula 900 (FIG. 9B), or longitudinally along the axis 918 of flow passage 920 between the catheter 910 and the cannula 900 (FIG. 9C), or a combination thereof. Flow straighteners 916 thus divide flow passage 920 between catheter 910 and cannula 916 into a number of radially or concentrically divided channels. Alternatively, flow straighteners 916 have a rectangular, square, triangular or hexagonal channel configuration, or another design. Flow straighteners 916 may also be utilized in combination with additional inlet and outlet holes, aperture or ports 909 and 911, as described above.

Flow straighteners 916 redirect swirl and other non-axial flow that is moving rotationally or circumferentially through passage 920 to axial flow, moving substantially along axis 918 through the different channels formed along flow passage 920. Flow straighteners 916 may be located along or across the proximal (inlet) end 914 of cannula 900 and catheter 910, along or across the distal (outlet) end 912 of cannula 900 and catheter 910, or at both ends 914 and 912.

Figure 10A:
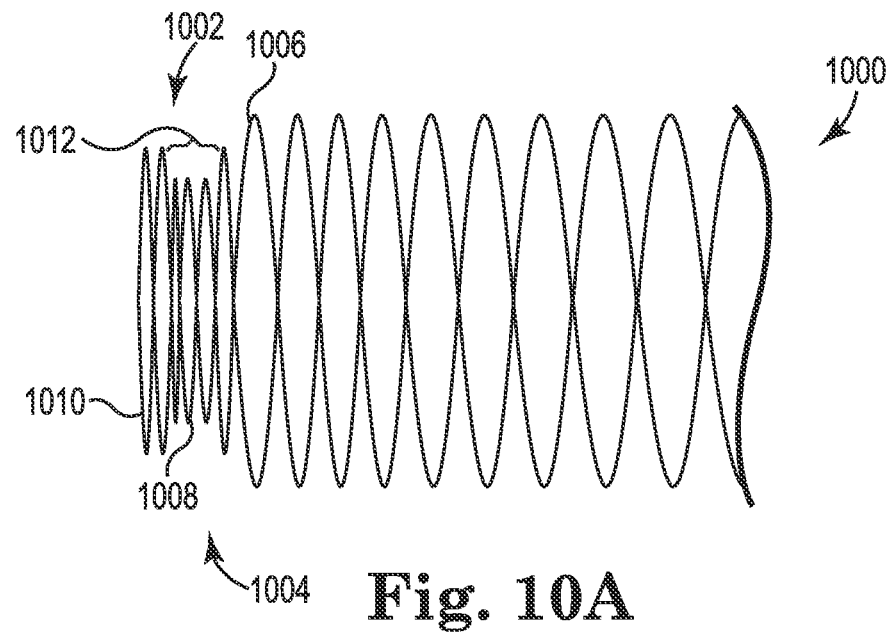
FIG. 10A is a side view of a cannula according to yet another embodiment of the present disclosure having a port fixation feature.
Figure 10B:
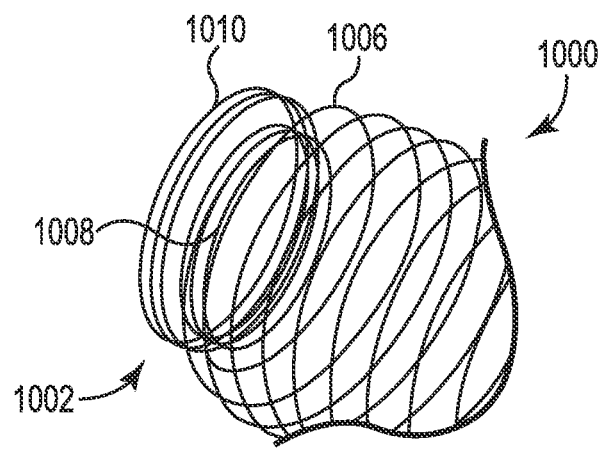
FIG. 10B is a perspective view of the cannula of FIG. 10A.

In still further embodiments, as illustrated in FIGS. 10A and 10B, a cannula 1000 may include one or more features 1002 for port fixation. More specifically, as shown in cross-section in FIG. 11A, where there is an opening 1102 in the wall 1103, for example but not limited to, between any combination of heart chamber(s) and blood vessel(s), the cannula 1000 may be configured such that it can be placed in the opening, expanded as described in various manners above, and remain substantially affixed with respect to the opening by means of the one or more features 1002 for port fixation, as illustrated in cross-section in FIG. 11B.

In one particular embodiment, one end of the cannula 1000, such as but not limited to, the distal end 1004, may include an impeller conduit section 1006, a neck section 1008, and a port fixation section 1010. As described with respect to the various cannula embodiments above, the cannula 1000, including the impeller conduit section 1006, neck section 1008, and a port fixation section 1010, may be adjusted between a collapsed, deployment configuration and an expanded, operable configuration.

As illustrated in FIGS. 10A and 10B, in the expanded, operable configuration, the neck section 1008 may be configured to expand to a diameter that is smaller than the expanded diameter of the impeller conduit section 1006 and the port fixation section 1010, thereby forming a generally hourglass shape having a pocket 1012 created between the impeller conduit section and the port fixation portion at the neck section.

Figure 11C:
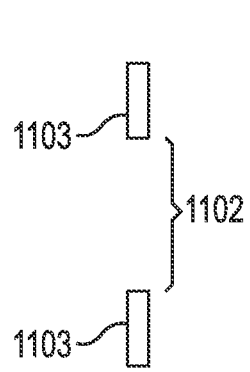
FIG. 11C is a side schematic view of the cannula embodiment of FIG. 10A fixed within the opening of FIG. 11A, wherein the opening also has an intermediate device fixed at the wall opening.
Figure 11C:
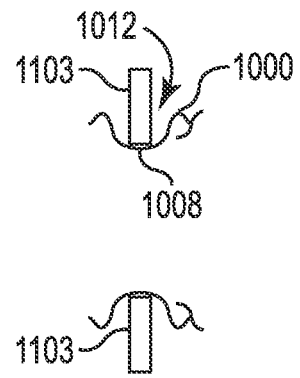
Figure 11C:
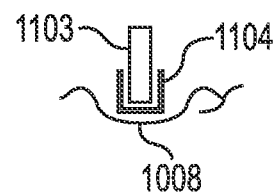
Figure 11C:
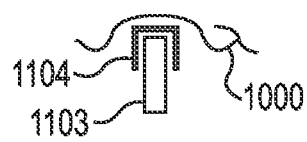

As illustrated in FIG. 11B, the cannula 1000 may be expanded at a position such that the pocket 1012 formed at the neck section 1008 upon expansion of the cannula may generally align with the wall opening 1102. The relatively larger diameters of the impeller conduit section 1006 and the port fixation section 1010 can be designed such that they do not easily pass through the wall opening 1102 when the cannula is in the expanded, operable configuration, and thus cause the cannula 1000 to remain substantially affixed with respect to the opening by means of the pocket 1012. In additional embodiments, as shown in FIG. 11C, an intermediate device 1104, such as a port or similar device, may be fixed at the wall opening 1102 to, for example only, improve the opening strength and/or improve the opening geometry.

The flexible film or mesh covers of the various embodiments of cannulas described above may be manufactured from any suitable materials, such as but not limited to a polymer, a metal or metal alloy, a shape memory material, or combinations of such materials. In further embodiments, the various cannulas described above may be provided without flexible film or mesh covers, thereby leaving the support members exposed. Alternatively, different cover or structural support materials may be provided, including, but not limited to: PTFE or ePTFE, HDPE or PEHD, PET or PETE, PU, polyimide, silicone materials, and combinations thereof.

The pump and impeller mechanisms, and the corresponding cannula and flow passage and channel structures, may also be fixed in anatomical position by a catheter support, by the cannula resting against a vessel wall or valve 1103, by a guidance feature resting against the internal or external anatomical structure of a heart, vein, artery, or blood vessel, by a coil anchor, or by inflating a balloon, for example between the cannula and a vessel wall, valve, or other anatomical structure 1103, as described above.

With reference again to FIG. 1, in one embodiment, the various embodiments of impellers and cannulas described in the present disclosure may be adjusted, for example to expand and retract the impellers and/or cannulas between the expanded, operable configuration and collapsed, deployment configuration, using a plurality of concentric layers or sheaths of the catheter, as will be described in further detail below. Generally, however, in various embodiments, the plurality of concentric layers may include a drive shaft layer, translatable along the catheter's axial direction for adjusting the impeller, and a cannula sheath, translatable along the catheter's axial direction for adjusting the cannula. In alternative or additional embodiments, the drive shaft layer and/or the cannula sheath may be rotatable about the axis of rotation, so as to permit, for example, variation in impeller blade angle and/or to assist in, for example, collapsing a spiral support member, flexible support member, flexible mesh or flexible mesh or support element cover, as described above.

Guidance

Figure 12:
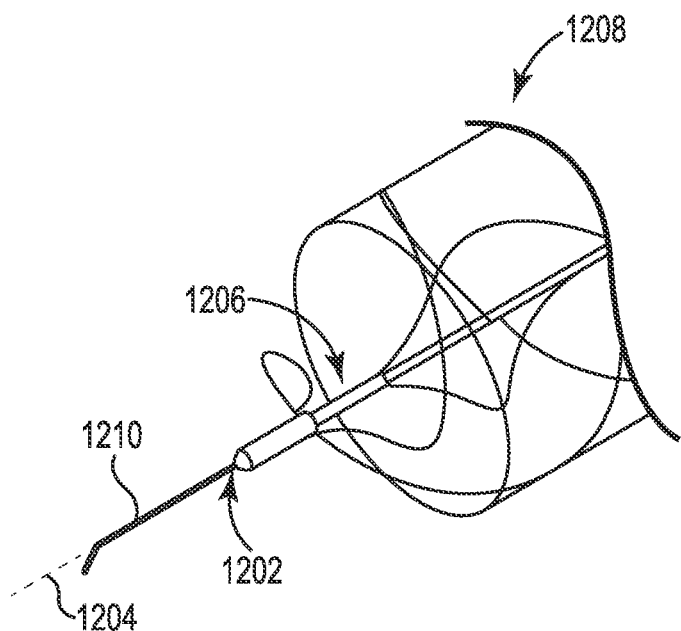
FIG. 12 is a perspective view of a catheter guidance system according to one embodiment of the present disclosure.

In general, the various embodiments of pumps disclosed herein may include a guidance system for directing the catheter and pump into and through the vasculature to the desired anatomical position, for example, at the heart. Suitable guidance systems, according to one embodiment of the present disclosure, illustrated in FIG. 12, may include an opening or passageway 1202 through or along the central axis 1204 of the catheter 1206, such that the catheter and pump 1208 may be inserted over and travel along a guidewire 1210 as will be understood by those skilled in the art.

Figure 13:
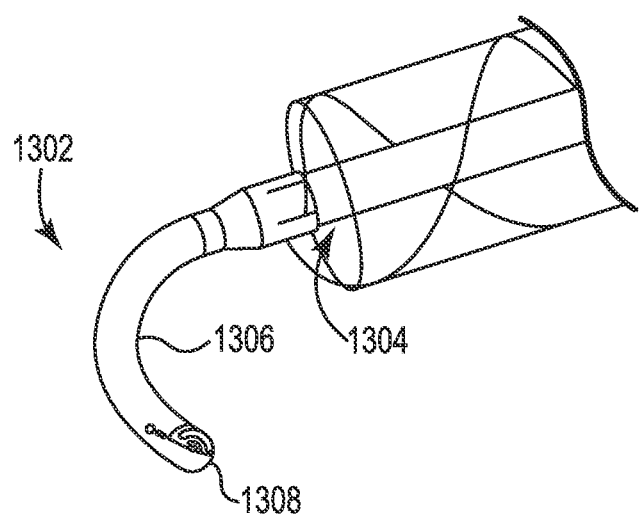
FIG. 13 is a perspective view of a catheter guidance system according to another embodiment of the present disclosure.

In another embodiment, illustrated in FIG. 13, a guidance system for directing the catheter and pump into and through the vasculature to the desired anatomical position may include a steerable catheter tip 1302. More specifically, the catheter 1304 may include a generally flexible section 1306 at or near its distal end. The flexible section 1306 may have an adjustable curvature that permits the flexible section of the catheter to be adjusted to aim the catheter in the desired direction of travel. In one embodiment, the flexible section 1306 may have a bias for curvature in a predetermined direction, or in some embodiments may have a bias for no curvature.

The flexible section 1306 may include a cable therewithin and anchored thereto for controlling the curvature of the flexible section, the cable running through the catheter to an external control system. In a particular embodiment, the cable is anchored at or near the tip 1308 of the flexible section 1306, which may permit ease of control. The cable may be used to control the flexible section 1306 by, for example, manipulating or pulling the cable at the external control system to cause a desired curvature of the flexible section. Similarly, when the cable is manipulated in a different direction or released, the flexible section 1306 may return to its normal biased position.

In any of these examples, placement aids, such as radio opaque marks, could be included near the pump or in other locations to assist in placement via fluoroscopy or other imaging technique. Alternatively, such placement aids, markers, or tags could be included in or provided on one or more of the pump, cannula, catheter, impeller or other structural element.

Power Transmission

In general, the various embodiments of pumps disclosed herein may include a power transmission system in the catheter for driving the impeller. The transmission system may be controlled, for example, from a control and/or power unit operably connected at or to an external end of the catheter. The power transmission system may generally provide for transferring power from the external control and/or power unit to the mechanical power needed by the pump or impeller.

Figure 14:
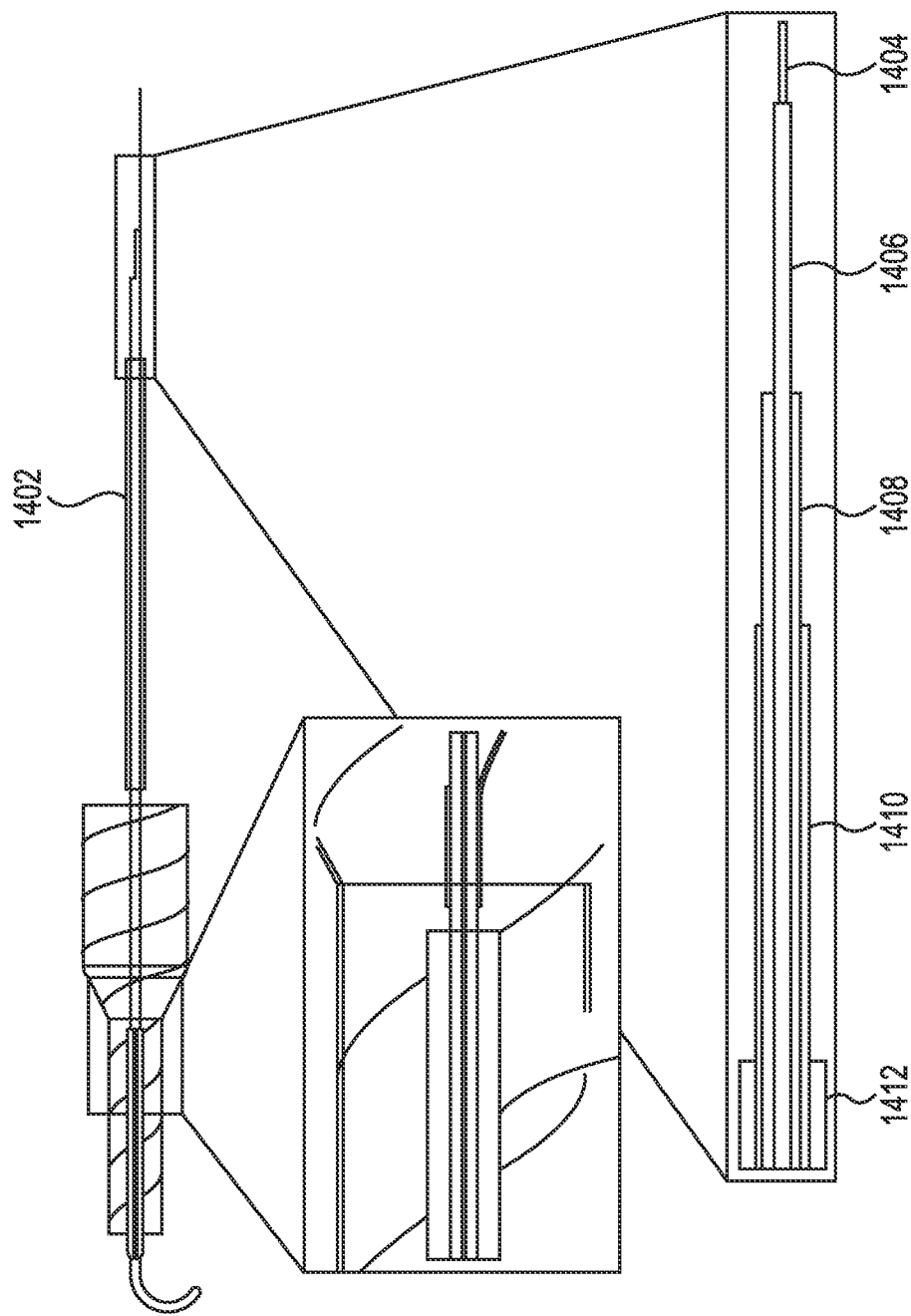
FIG. 14 includes a side view and exploded side views of a power transmission system of a pump according to one embodiment of the present disclosure.

In one embodiment, as illustrated in FIG. 14, the transmission system may include a drive shaft that connects the impeller directly with a drive motor of the control and/or power unit through a clutch. In one embodiment, as described briefly above, the catheter 1402 may include a plurality of concentric layers. In one such embodiment, these layers in order of innermost to outermost, may include but are not limited to, a cable 1404, an inner catheter sheath 1406, a rotatable layer 1408 of the drive shaft, a drive shaft layer 1410 that is axially positionable with respect to the rotatable layer 1408 and may, in some embodiments, be rotatable therewith, and an axially positionable cannula sheath 1412.

The cable 1404 may be used, for example, to control the guidance system, such as a steerable catheter tip, described above; however, in other embodiments, the cable 1404 may be eliminated leaving a passageway for a guidewire along which the catheter travel may travel. The inner catheter sheath 1406 may surround the cable 1404. The rotatable drive shaft layer 1408 may provide the rotational motion for the impeller and transfer the rotational motion thereto.

The drive shaft layer 1410, which is axially positionable with respect to the rotatable layer 1408, may be used, as described above, to retract and deploy any of the impeller embodiments of the present disclosure. The cannula sheath 1412 may be axially positionable with respect to the inner catheter sheath 1406 and may be used, as described above, to retract and deploy any of the cannula embodiments of the present disclosure. The outer sheath 1406 may include an embedded braid or other structural element to increase torque transfer, or a coil to improve kink resistance, or both.

In one or more embodiments, the drive shaft layers 1408, 1410 may be longitudinally flexible, but torsionally rigid, thereby permitting the drive shaft to have flexibility when be maneuvered through the vasculature, but maintaining ability for delivering rotational motion. The drive shaft and drive shaft layers 1408, 1410 may be constructed of a single or multi-filar coil (or thread or fiber) construction.

The hollow center of a catheter element, for example inner catheter sheath 1406 or drive shaft layer 1408 or 1410, could allow a guidewire to pass. There could also be a short rigid section to attach the pump.

One or both of the drive shaft layers 1408, 1410 may be lubricated with a lubricating fluid, such as but not limited to saline. The construction may also use low friction coatings, such as Teflon, between relatively moving or rotating layers or elements, for example sheath layers, guide wires, cables, and shaft layers. The rigid section may further be supported by mechanical bearings, such as ball, hydrodynamic or plain bearings. The rotatable drive shaft layer 1408 or both drive shaft layers 1408, 1410, as thus described, may be used to control the pump by delivering or transferring rotational motion to the impeller.

Figure 15:
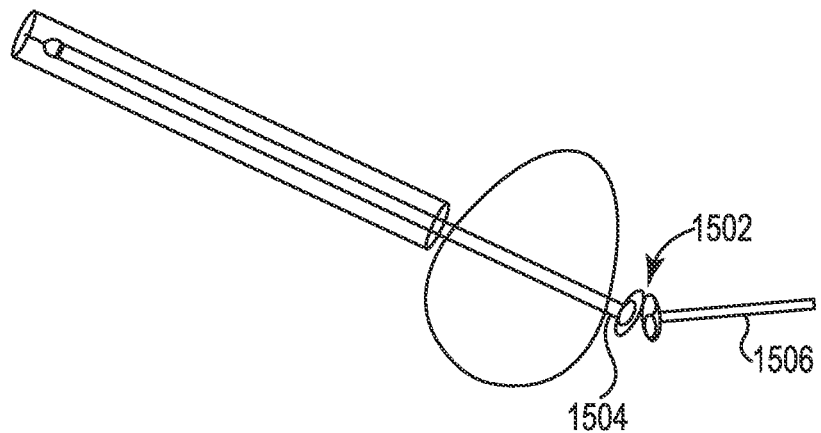
FIG. 15 is a perspective view of a power transmission system of a pump according to another embodiment of the present disclosure.

In a further embodiment, illustrated in FIG. 15, the transmission system may include drive shaft element generally configured as that described above, except that at one or more locations along the drive shaft, a set of gears 1502 may be employed to permit relatively sharper bends or angles in the drive shaft between a distal drive shaft section 1504 and a proximal drive shaft section 1506, while maintaining torque along the drive shaft. In some embodiments, the drive shaft sections 1504, 1506, with gears 1502 at their adjacent ends can be brought into contact with one another or maintain contact with one another via tensioning element, such as but not limited to a cable or sheath. The angle between the drive shaft sections 1504, 1506 may be adjustable.

Figure 16:
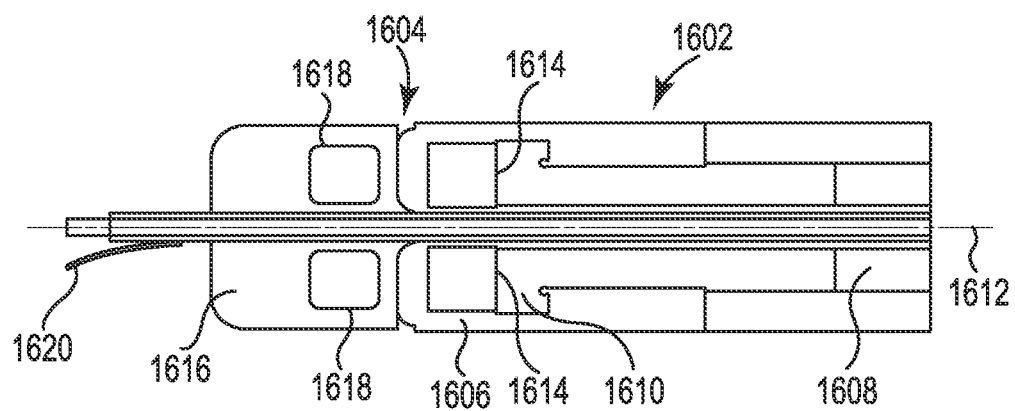
FIG. 16 is a perspective view of a power transmission system of a pump according to still a further embodiment of the present disclosure.

In another embodiment, illustrated in FIG. 16, the transmission system may include a fluid driven or hydrostatic transmission system 1602 in combination with a magnetic coupling device 1604. In general, an external system may drive a fluid to a mechanical generator, causing rotational motion of the mechanical generator, which is transferred to the impeller via a magnetic couple. In a particular embodiment, the hydrostatic transmission system 1602 may include a catheter body or outer sheath 1606 and an inner sheath 1608, concentrically positioned within the outer sheath, the distal ends of which are operably connected with a mechanical generator 1610.

The inner sheath 1608 may provide an inlet channel or lumen by which to deliver fluid from the external system to the mechanical generator 1610, while the outer sheath 1606 may provide an outlet channel or lumen by which to return fluid from the mechanical generator to the external system; of course, in other embodiments, the outer sheath may provide the inlet channel while the inner sheath may provide the outlet channel. The mechanical generator 1610 may convert the axial motion of the fluid passing therethrough to rotational motion of the generator about the central axis 1612 of the catheter.

At or near a distal end of the generator 1610, the generator may include a proximal end of the magnetic coupling device 1604, including one or more magnets 1614. The magnets 1614 may, by means of the rotational motion of the generator, also rotate therewith about the central axis 1612 of the catheter, creating a changing magnetic field at the distal end of the mechanical generator 1610.

Positioned at or near the distal end of the hydrostatic transmission system 1602 may be the distal end of the magnetic coupling device 1604 having a housing 1616 also including one or more magnets 1618 which interact with the magnets 1614 of the proximal end of the magnetic coupling device to cause rotational motion of housing 1616. More specifically, the changing magnetic field created by the rotational motion of magnets 1614 of the proximal end of the magnetic coupling device 1604 interacts with the magnets 1618 in housing 1616 causing rotational motion thereof.

An impeller 1620, such as any of the various embodiments of impellers described herein, may be operably connected with the distal end of the magnetic coupling device 1604 or housing 1616 and thus rotate therewith. One advantage of such fluid driven or hydrostatic transmission system 1602 in combination with a magnetic coupling device 1604 is impeller interchangeability since the indirect connection provided by the magnetic coupling device between the transmission system and the impeller provides a relatively easy interconnect for changing between impeller embodiments.

Figure 17:
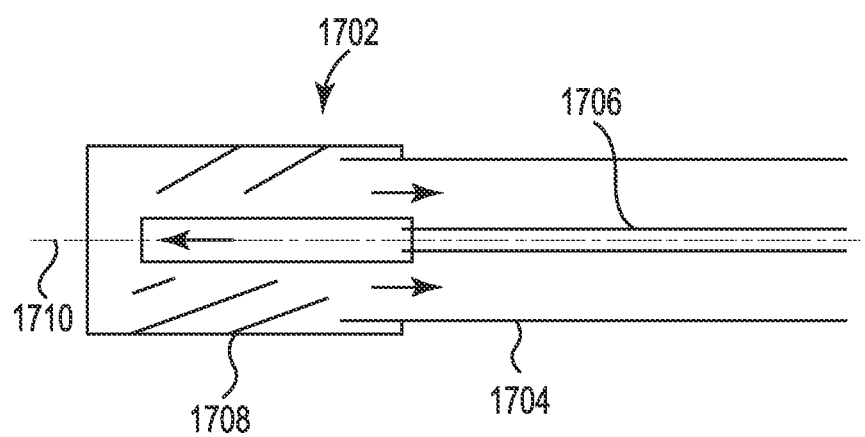
FIG. 17 is a perspective view of a power transmission system of a pump according to yet another embodiment of the present disclosure.

In another embodiment, illustrated schematically in FIG. 17, the transmission system may simply include a fluid driven or hydrostatic transmission system 1702 driving an operably connected impeller. In general, an external system may drive a fluid to a mechanical generator, causing rotational motion of the mechanical generator, which is transferred substantially directly to the impeller. In a particular embodiment, the hydrostatic transmission system 1702 may include a catheter body or outer sheath 1704 and an inner sheath 1706, concentrically positioned within the outer sheath, the distal ends of which are operably connected with a mechanical generator 1708.

The inner sheath 1706 may provide an inlet channel or lumen by which to deliver fluid from the external system to the mechanical generator 1708, while the outer sheath 1704 may provide an outlet channel or lumen by which to return fluid from the mechanical generator to the external system; of course, in other embodiments, the outer sheath may provide the inlet channel while the inner sheath may provide the outlet channel. The mechanical generator 1708 may convert the axial motion of the fluid passing therethrough to rotational motion of the generator about the central axis 1710 of the catheter. The mechanical generator 1708 may be directly connected to the impeller, such as any of the various embodiments of impellers described herein; however, it is recognized that any suitable elements for indirectly or operably connecting the mechanical generator 1708 and impeller, such as but not limited to a gearing system, are within the spirit and scope of the present disclosure.

With respect to the various fluid driven or hydrostatic transmission systems described above, a fluid driven or hydrostatic transmission system may be externally connected with, for example, a hydraulic connector or compressible tube, which mates the fluid driven or hydrostatic transmission system to an external controller for driving the fluid, as will be understood by those skilled in the art. The external controller may or may not be a component of the control and/or power unit, described herein.

In yet another embodiment, the transmission system may be electrically driven. More specifically, the impeller, such as any of the various embodiments of impellers described herein, may be operably connected with a motor at or near the pump end of the catheter. An electrical system may be driven by the control and/or power unit operably connected at or to an external end of the catheter and may condition the energy for use in controlling the motor and rotating the impeller, as will be recognized by those skilled in the art.

The electrical system, or a portion thereof, may be located at or near the motor or may be positioned at any other suitable location, including but not limited to at the control and/or power unit operably connected at or to an external end of the catheter. The electrical system and control and/or power unit may be operably connected by means of electrical connectors or conductors.

Figures 18, 19:
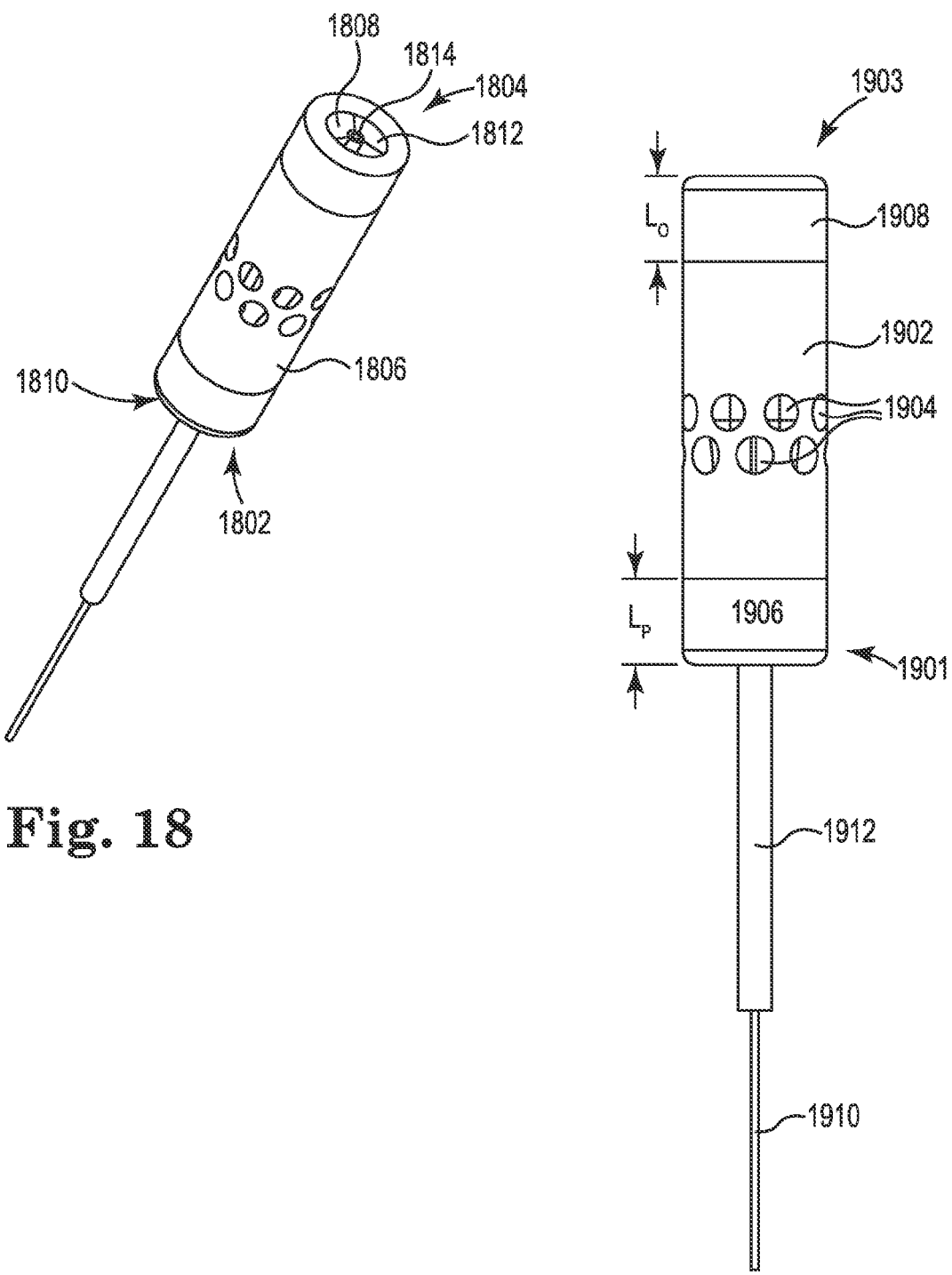
FIG. 18 is a perspective view of an expandable blood pump according to one embodiment of the present disclosure.
FIG. 19 is a side view of the expandable blood pump shown in FIG. 18.

FIGS. 18 and 19 depict an alternative embodiment of the expandable blood pump of the present disclosure. The expandable blood pump of FIGS. 18 and 19 is particularly suitable for use with the right portion of the heart, in that the blood pump has a proximal inlet 1802 and a distal inlet 1804. The cannula 1902 has a lateral cannula exterior 1806 with at least one lateral opening 1904 to function as one or more outlets. In operation, blood enters the expandable blood pump at the proximal inlet 1802 at proximal end 1901, at the distal inlet 1804 at distal end 1903, or both, and exits the expandable blood pump through the outlet of the at least one lateral opening 1904. Thus, cover or cannula 1902 may permit blood flow to exit the expandable blood pump at a direction that is transverse, generally transverse, or substantially perpendicularly to the impeller axis. Blood flow through the at least one lateral opening 1904 increases the pressure of the blood in the right heart, causing the blood to flow from the right heart so as to travel to the lungs and enter the cycle of pulmonary circulation.

In further embodiments, the expandable blood pump may have a proximal expandable member 1906 at the proximal inlet 1802, a distal expandable member 1908 at the distal inlet 1804, or both. Each expandable member 1906, 1908 may be configured to increase in exterior size, such as in diameter, or around some or all of its circumference, so that it can engage with an anatomical structure. In some embodiments, the expandable members 1906, 1908 may be configured to engage with blood vessels. For example, the expandable members 1906, 1908 may be configured to engage with blood vessels such as the aorta, vena cavea, the superior vena cava, the inferior vena cava, other vessels, or combinations of these. In other embodiments, the expandable member may engage with other or additional structures in the body, or in the heart, such as one or more valves in the heart. The expandable member may engage with the tissue structure in such a manner as to reduce, substantially reduce, substantially prevent, or prevent blood flow between, by, or around the exterior of the expandable member and the tissue structure with which the exterior of the expandable member is engaged.

In some embodiments, the expandable members 1906, 1908 are configured to be positioned between a deployment configuration, which is generally collapsed for reduced or minimal size, and an operable configuration, in which the expandable member is partially or wholly expanded in size. In some embodiments, the expandable member may be expanded by being inflated with a fluid, such as air, saline, other physiological compatible fluid, or combinations of these. Where inflation is used, the inflation may be done by a local pump, by a separate conduit that is operably connected with an external control unit, or a combination. The expandable members 1906, 1908 may be operably connected, such as by a passage, so that inflation of one results in inflation of both, or they may be separately inflatable and adjustable. In other embodiments, the expandable member may be expanded by other mechanisms, such as mechanically, including by the use of biased members. In other embodiments, the expandable member may be maintained in a constrained configuration when in the deployment configuration, such as by being restrained by a restraining member, such as a sheath. When the sheath or other restraining member is disengaged from the expandable member, the expandable member expands to a size that is greater than the size of the expandable member when in its deployment configuration. In still other embodiments, the expandable member may be maintained mechanically in a deployment configuration, such as by gears that engage with slots in the expandable member, where the gears are driven by a drive mechanism. In such embodiments, the drive mechanism can be used to expand or contract the expandable member by any desired extent.

In some embodiments, the expandable members 1906, 1908 may be provided with an aperture, to operate as an inlet to the pump. Thus, proximal expandable member 1906 may be provided with proximal expandable member aperture 1808, distal expandable member 1908 may be provided with distal expandable member aperture 1810, or both expandable members 1906, 1908 may be provided with an aperture. In some embodiments, the size of one or both of the apertures 1808, 1810 may be fixed. In some embodiments, the size of one or both of the apertures 1808, 1810 may be selectively adjustable, so as to help monitor or control blood flow through one or both of the apertures 1808, 1810. Thus, in use, one or both of the apertures 1808, 1810 may be expanded, one or both of the apertures may be contracted, one aperture may be unchanged while the other is either expanded or contracted, or one aperture may be expanded while the other is contracted. This selective control over aperture size enhances the ability of the expandable blood pump of the present disclosure to appropriately regulate blood flow, to obtain a desired flow of blood through the superior vena cava, and a potentially different flow of blood through the inferior vena cava.

In other embodiments, one or both of the expandable members 1906, 1908 may each comprise two or more operably adjoined or positioned expandable members, or one or more fixed members operably adjoined with one or more expandable members. For example, in one embodiment, an expandable member 1906 (or an expandable member 1908, or both) can be two or more concentric expandable members shaped as rings or doughnuts; in such a configuration, an inner ring can be expandable to a fixed configuration while an outer ring can be expandable to an adjustable configuration, or vice versa, or both can be expandable to a fixed configuration or both can be expandable to an adjustable configuration. In other embodiments, an expandable member 1906, 1908 can be configured in some other desirable manner, such as in a U-shaped or other offset or irregular configuration. In other embodiments, an expandable member 1906, 1908 could be provided as a foam, polymeric, or other elastic segment provided in a C shape, with an expandable portion that is positioned in the open portion of the C so as to contact one or both of the ends of the C when expanded. Any other desired configuration can be used for the expandable member 1906, 1908.

In one embodiment, the proximal expandable member 1906 may be positioned and configured to engage with the inferior vena cava. In another embodiment, the distal expandable member 1908 may be positioned and configured to engage with the superior vena cava. In another embodiment, the proximal expandable member 1906 may be positioned and configured to engage with the inferior vena cava and the distal expandable member 1908 may be positioned and configured to engage with the superior vena cava. Where the proximal expandable member 1906 is engaged with the inferior vena cava and the distal expandable member 1908 is engaged with the superior vena cava, the expandable blood pump can be situated so as to control all or substantially all of the blood flow into the right portion of the heart.

In other embodiments, an expandable ring may be positioned on or outside one or more expandable members 1906, 1908 to help prevent blood flow on the outside of the expandable blood pump. The ring may include a membrane securely attached to the ring. The ring may be attached to one or more of the expandable members 1906, 1908, the cannula, other portions of the expandable blood pump, or combinations of these. In a deployment configuration, the ring (and membrane) may be constrained near or on the expandable blood pump. In the operable configuration, the ring would expand and interface with surrounding tissue, to provide a partial or complete seal, thus helping direct blood through the pump.

The at least one lateral opening 1904 is depicted in FIGS. 18 and 19 as a series of holes. In other embodiments, there may be any number of lateral openings 1904. In still other embodiments, the lateral openings 1904 may be of any desired shape and size. In other embodiments, the cannula 1902 may be made of a porous or mesh material, with a large number of pores or openings. In still other embodiments, cannula 1902 is not present, while in other embodiments that may or may not have cannula 1902 support ribs connect proximal inlet 1802 and distal inlet 1804.

As can be seen in FIGS. 18 and 19, the expandable blood pump can contain many of the components discussed above, such as driveshaft 1910, catheter 1912, etc. A support member 1812 can be positioned so as to suspend the axis of rotation of the impeller generally in the center of the expandable members 1906, 1908. The support member 1812 can be formed of spokes, such as Nitinol, or other polymeric or other suitable material. In one embodiment, the support member 1812 is a series of flexible segments or strands, so that when the axis 1814 is moved in one direction, a segment or strand on the other side is put into tension, and a segment or strand in the direction of the force of the axis 1814 may be put into compression, or both, in order to maintain the position of the axis 1814. Any desired configuration of support member 1812, with any suitable number or form of segments or strands, may be used.

The length of the cannula 1902 may be axially adjustable, as described above with respect to FIGS. 4, 5, and 6. In other embodiments, the cannula 1902 may comprise telescoping, overlapping sections, one sliding over the other, to allow for axial adjustment of the length of the expandable blood pump. In other embodiments, the cannula 1902 made be made of a material that is sufficiently elastic to stretch and contract, to allow for axial adjustment of the length of the expandable blood pump.

In some embodiments, in addition to or instead of having the length of the expandable blood pump being axially adjustable, the length $L_D$ as shown in FIG. 19 of the distal expandable member 1908, the length $L_P$ as shown in FIG. 19 of the proximal expandable member 1906, or both, may be sufficient to ensure at least partial insertion into the opposed vena cavae of the right heart, so that the distal expandable member 1908 is positioned at least partially within the superior vena cava, the proximal expandable member 1906 is positioned at least partially within the inferior vena cava, or both. In some embodiments, the length $L_D$ of the distal expandable member 1908, the length $L_P$ of the proximal expandable member 1906, or both may be adjustable in an axial direction, by one or more ways described above with regard to radial expansion. Axial expansion of one or both of the expandable members 1906, 1908, allows the extent of insertion of one or both of the expandable members 1906, 1908 into the opposed vena cavae to be calibrated or adjusted to a desired extent, such as to accommodate different size hearts. In still other embodiments, the expandable blood pump of the present disclosure may be provided in different lengths, so that an expandable blood pump of a suitable or desired size or length can be selected for use with a given size right heart of a given patient.

In some embodiments, the expandable heart pump of the present disclosure has two inlets that are positioned opposite from one another, at opposite ends of the cannula 1902. In other embodiments, the expandable heart pump of the present disclosure may have one inlet, such as where one end of the cannula 1902 is closed off. In other embodiments, additional inlets may be provided, such as via ducts or tubes that are connected with the expandable heart pump. Where ducts or tubes are used, they may have any suitable angle with the cannula 1902, where a cannula 1902 is used. In other embodiments, the cannula 1902 may have branches or other passages that act as inlets. In other embodiments, holes or pores in the cannula 1902 may act as inlets. In other embodiments, a distal end of the expandable heart pump may act as one inlet, and the proximal end of the expandable heart pump acts as an outlet, or vice versa.

Figure 20:
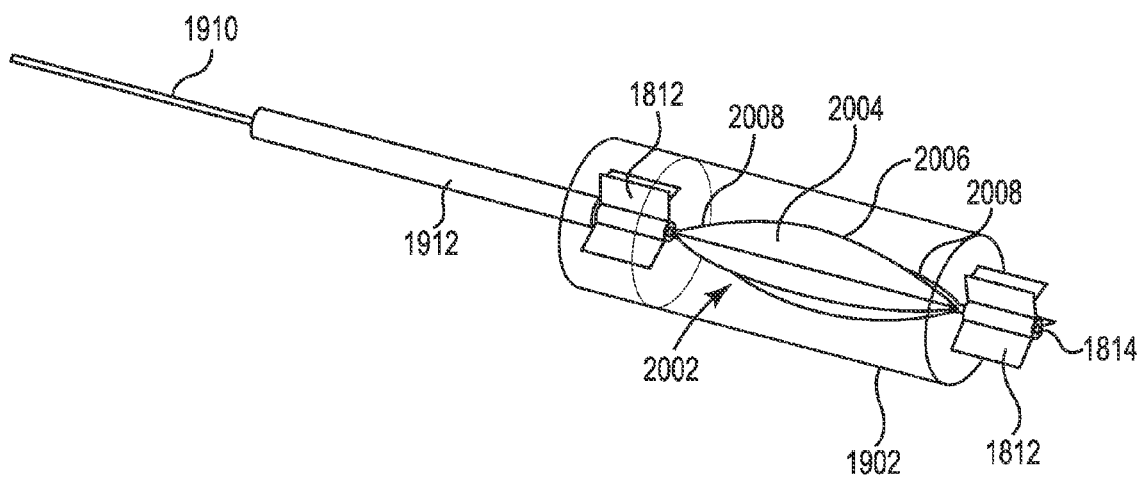
FIG. 20 is a perspective view of an expandable blood pump according to one embodiment of the present disclosure, with certain portions depicted in a translucent manner.
Figure 21:
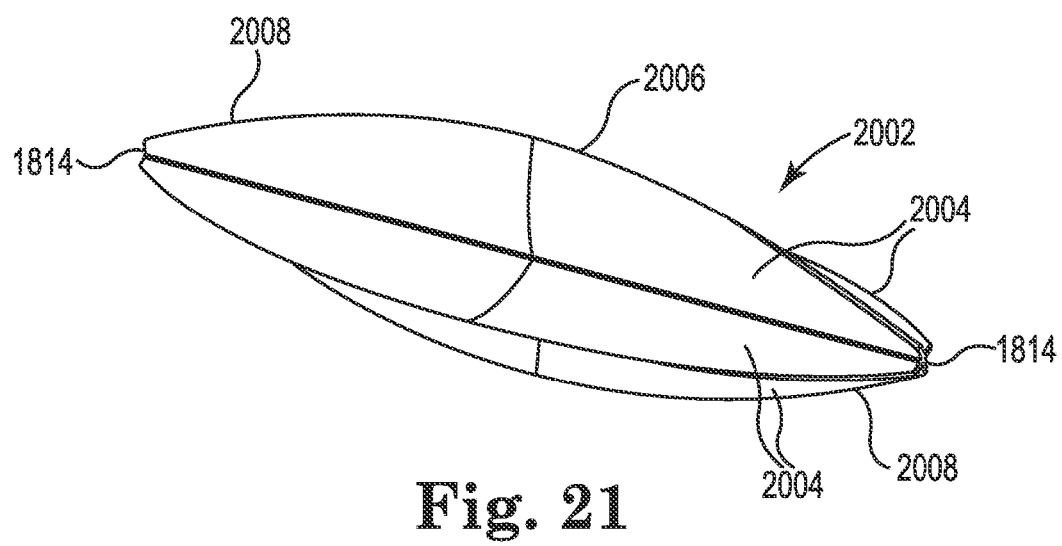
FIG. 21 is a perspective view of an impeller according to one embodiment of the present disclosure.

FIG. 20 shows a perspective view of the expandable blood pump of the present disclosure, with cannula 1902 depicted in a translucent manner, and with other components that are depicted in FIGS. 18 and 19 shown in FIG. 20 using like reference numerals. FIGS. 20 and 21 depict impeller 2002, which has at least one impeller blade 2004, though four impeller blades 2004 are depicted in FIGS. 20 and 21. Each impeller blade 2004 can be flat, or curved or otherwise shaped, as desired, including so that the blades form a spiral or other configuration when viewed from a cross-sectional perspective, looking at a plane that is perpendicular to the axis of rotation 1814. As can be seen, the impeller 2002 in the configuration of FIGS. 20 and 21 forms a centrifugal blood pump. Impeller 2002 can be shaped in any desired configuration, with any desired number of blades 2004. As depicted in FIGS. 20 and 21, the profile of the blades 2004 of impeller 2002 may be arcuate, so that the edges of the blades 2004 in the center region 2006 extends farther from the axis of rotation 1814 of the impeller 2002 than do the edges of the blades 2004 toward in the end regions 2008 of the impeller 2002. Having the blade edges extend further from the axis of rotation 1814 in the center region 2006 than toward the end regions 2008 may help to enhance blood flow from the proximal end 1901 and distal end 1903 of the expandable blood pump though the at least one lateral opening 1904 in the cannula 1902.

The impeller may have any other suitable profile. In one embodiment, the profile is generally even or level, as shown in FIG. 3. In another embodiment, the center region of the blades is closer to the axis of rotation than the end regions are. Still other embodiments of the profile are as shown in FIGS. 21A-21D. Any suitable impeller blade profile is within the scope of the present invention. The embodiment depicted in FIG. 21B contains multiple smaller blades, which may be staggered around the impeller's axis of rotation.

Generally, for use with right heart pumps, including centrifugal pumps for use in the right hear, the pump will create a flow of blood that is generally transverse with the impeller's axis of rotation (including in some embodiments through a side of a cannula or cover), rather than a flow of blood that would be generally in the axial direction, as would result from use of the impellers in FIGS. 4-7 and otherwise.

The centrifugal impellers of the present invention may use any suitable number of blades, from one, to two, or more. That certain examples of the present invention use four blades is not to be construed as limiting. In some embodiments, the impeller will have multiple blades, some or all of which are not the same length and/or do not run the length of the cannula, where the blades may be staggered around the axis of rotation, or arranged in some other desired configuration.

Figure 22:
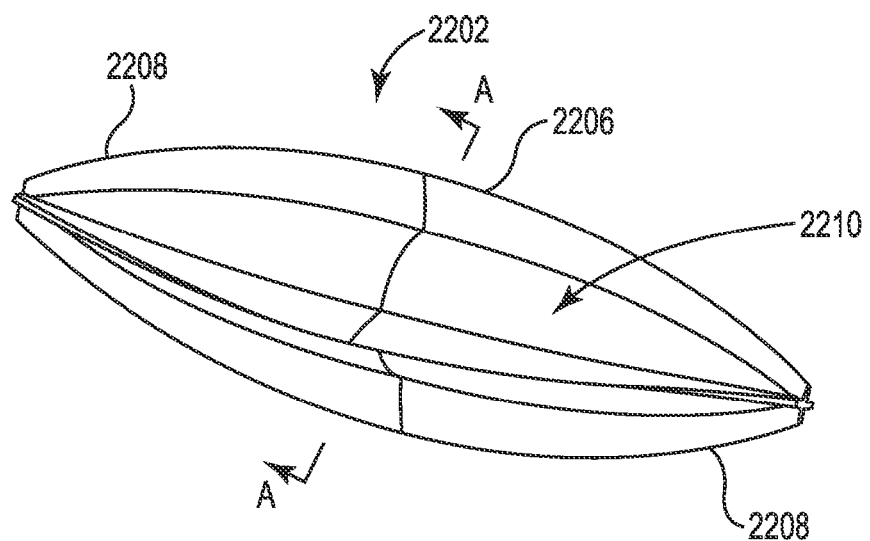
FIG. 22 is a perspective view of an impeller according to another embodiment of the present disclosure.
Figure 21A:
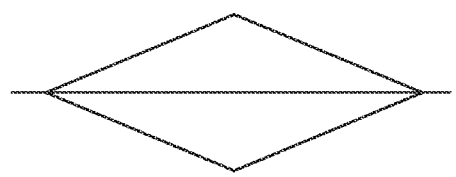
FIGS. 21A-21D show side views of other impellers of the present invention.
Figure 21B:
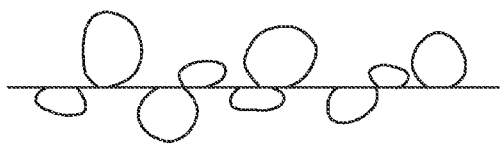
Figure 21C:
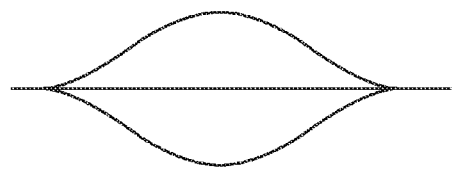
Figure 21D:
Figure 23:
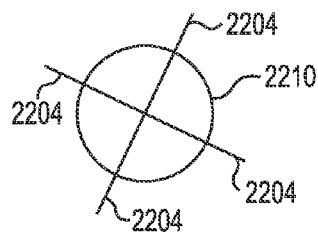
FIG. 23 is a cross-sectional view of the impeller of FIG. 22, taken along line A-A.
Figures 24, 25:
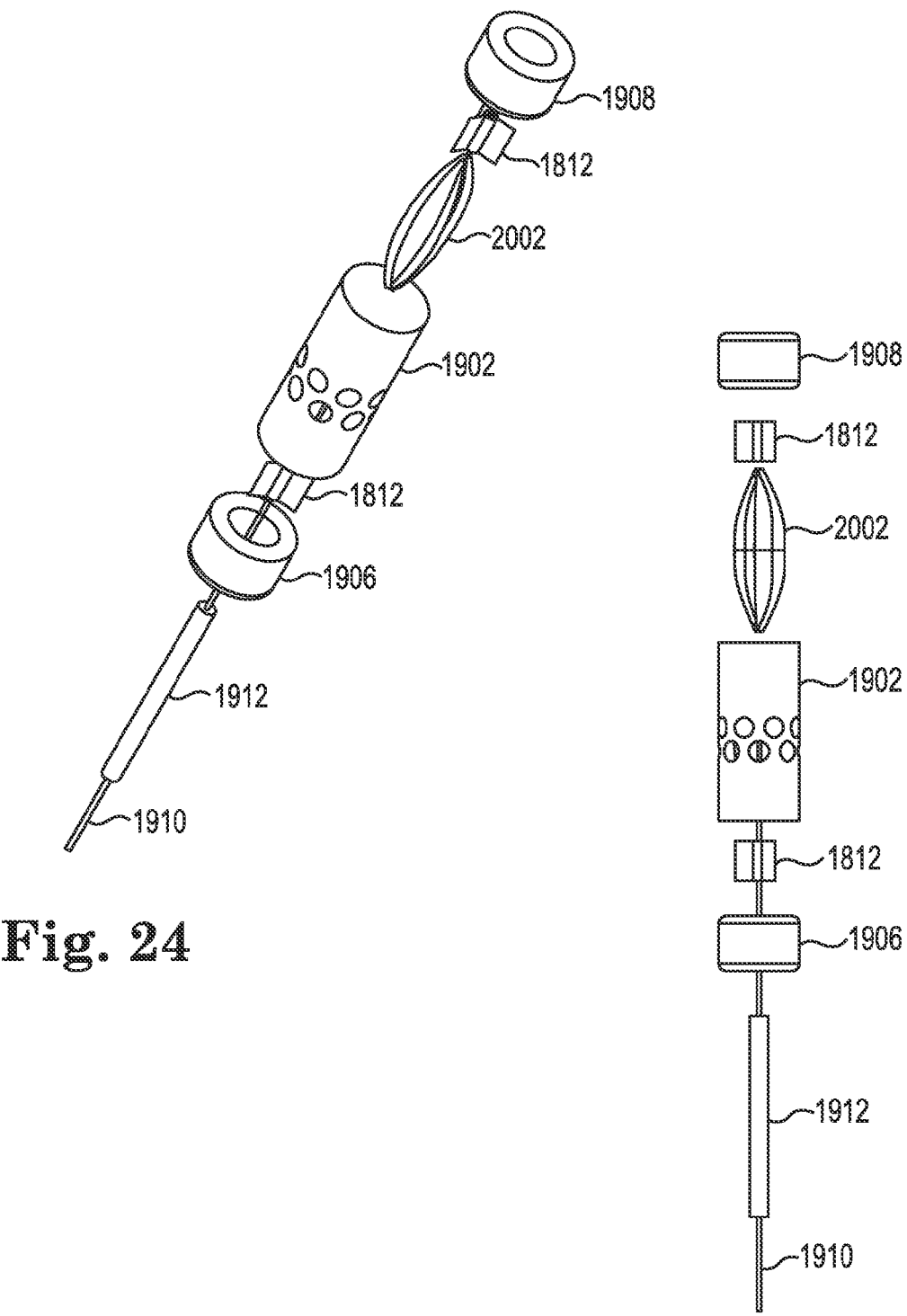
FIG. 24 is an exploded perspective view of an expandable blood pump according to one embodiment of the present disclosure.
FIG. 25 is a side view of the expandable blood pump shown in FIG. 24.
Figure 26:
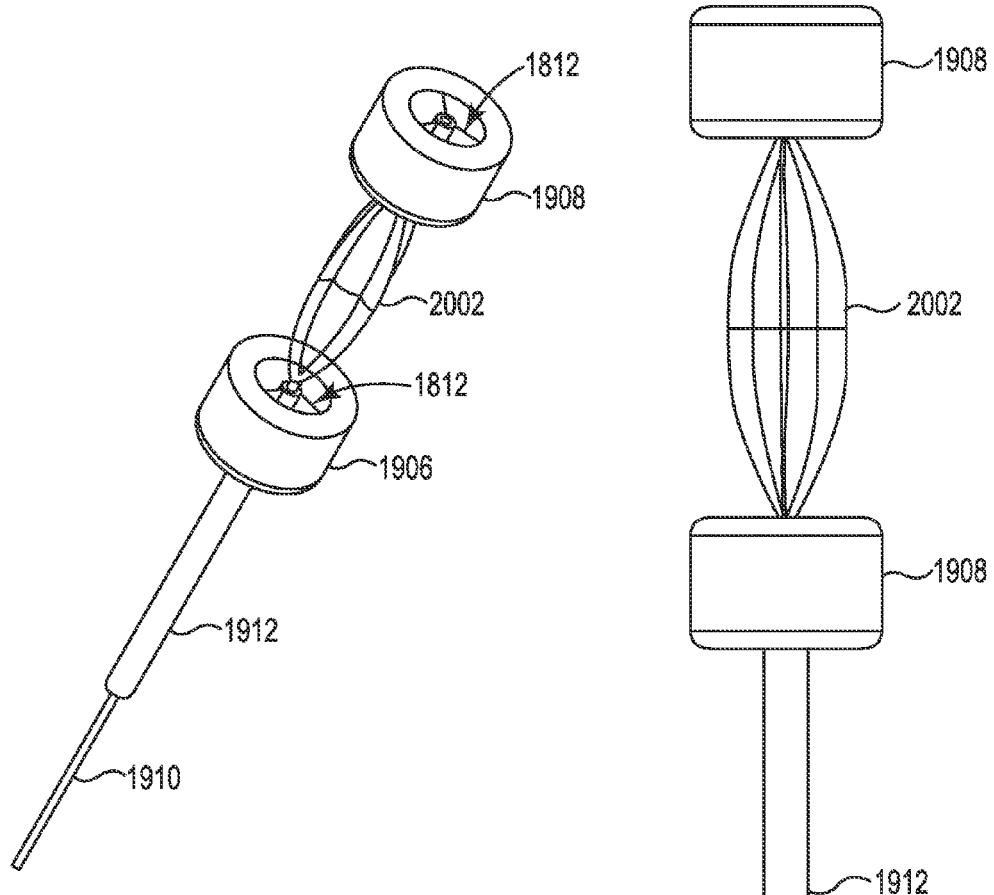
FIG. 26 is a perspective view of certain components of an expandable blood pump according to one embodiment of the present disclosure.
Figure 27:
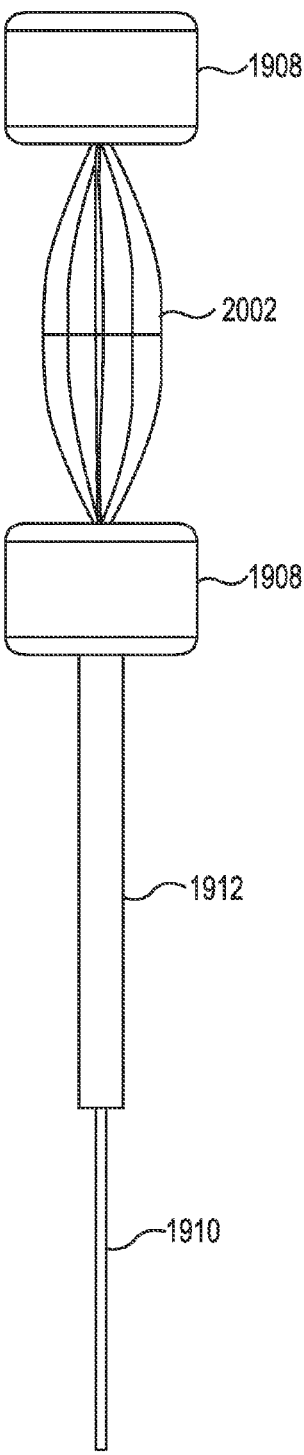
FIG. 27 is a side view of the certain components of an expandable blood pump shown in FIG. 26.

FIGS. 22 and 23 show another embodiment of impeller 2202 for use with the expandable blood pump of the present disclosure. The impeller 2202 has a center region 2206 that extends farther from the axis of rotation 1814 of the impeller 2202 than do the edges of the blades 2204 toward the end regions 2208 of the impeller 2202. Impeller 2202 further contains an impeller core region 2210, which extends outwardly from the axis of rotation 1814, as shown in FIG. 23. Impeller core region 2210 helps prevent blood from collecting, pooling, stagnating, or clotting near the axis of rotation 1814.

Impeller 2202 may be positioned while in a collapsed orientation. In some embodiments, impeller core region 2210 is expanded by having liquid (such as air, saline, or other physiological compatible fluid) inserted therein, while in other embodiments, impeller core region 2210 is expanded mechanically, including by having supports biased in an expanded state.

The impellers 2002 of the present invention can be made of any suitable materials, as described above. For example, in some embodiments, the impellers 2002 are made up of a material that does not use a support member or mast, such as where the blade 2004 is a collapsible, foldable, expandable, or inflatable section of polymer, web, Nitinol or another memory metal, or another biologically suitable material, or a composite or combination of these. In other embodiments of impellers 2002 disclosed herein, the impeller 2002 may be activated between a collapsed, deployment configuration and an expanded, operable configuration by changing the position of the blades 2004, by inflating the impeller, or by restraining the blades or allowing them to unfold or expand into their operable configuration of increased or maximum size.

Figures 28, 29:
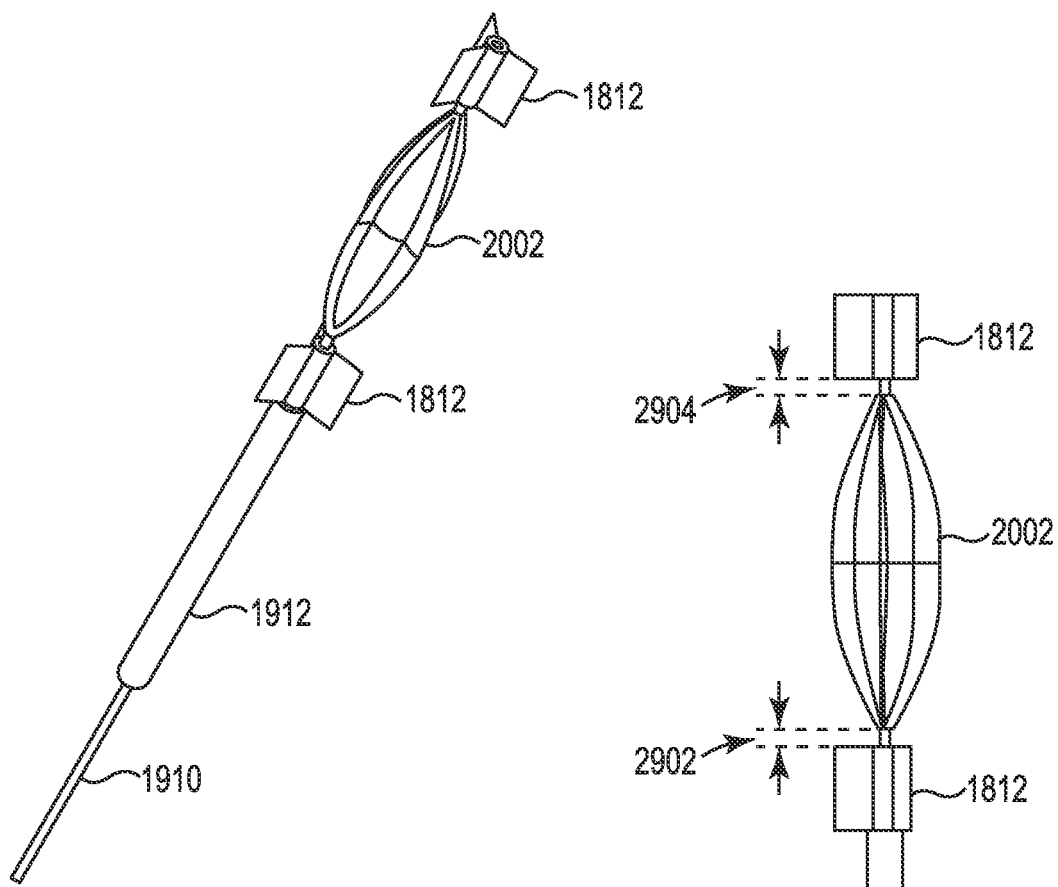
FIG. 28 is a perspective view of certain components of an expandable blood pump according to one embodiment of the present disclosure.
FIG. 29 is a side view of the certain components of an expandable blood pump shown in FIG. 28.

FIGS. 24-29 provide other views of an expandable heart pump of the present invention, with detail shown on types and various arrangements of components. FIG. 29 further shows proximal impeller spacing gap 2902 and distal impeller spacing gap 2904. As depicted, proximal impeller spacing gap 2902 and distal impeller spacing gap 2904 can be fairly small, and can be roughly the same. In other embodiments, proximal impeller spacing gap 2902 and distal impeller spacing gap 2904 may be any desired length, and they may be generally the same or they may be different, for example, such that either proximal impeller spacing gap 2902 is greater than distal impeller spacing gap 2904, or proximal impeller spacing gap 2902 is less than distal impeller spacing gap 2904. Arranging the impeller so that it is axially adjustable, in that the spacing gaps 2902 and 2904 are not the same but can be adjusted, allows the impeller to located closer to the inferior vena cava than to the superior vena cava, or closer to the superior vena cava than the inferior vena cava, as desired. Having the impeller be axially adjustable allows for relative adjustments between the pump's inlets. Where the adjustable blood pump of the invention is used as a right heart pump, having the impeller be axially adjustable allows for adjustments between the flow rates from the superior vena cava, the inferior vena cava, both, and relative adjustments between the two.

Figure 30:
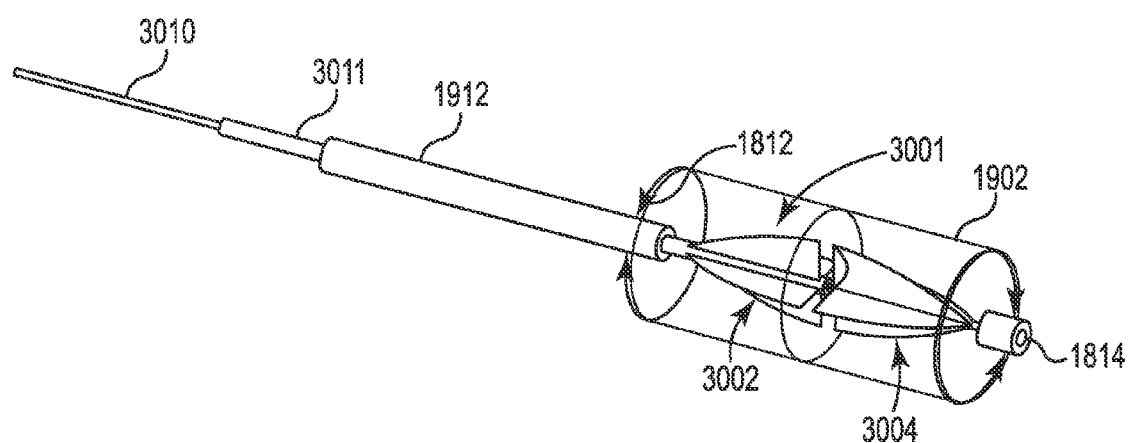
FIG. 30 is a perspective view of an expandable blood pump according to one embodiment of the present disclosure, with certain portions depicted in a translucent manner.
Figure 31:
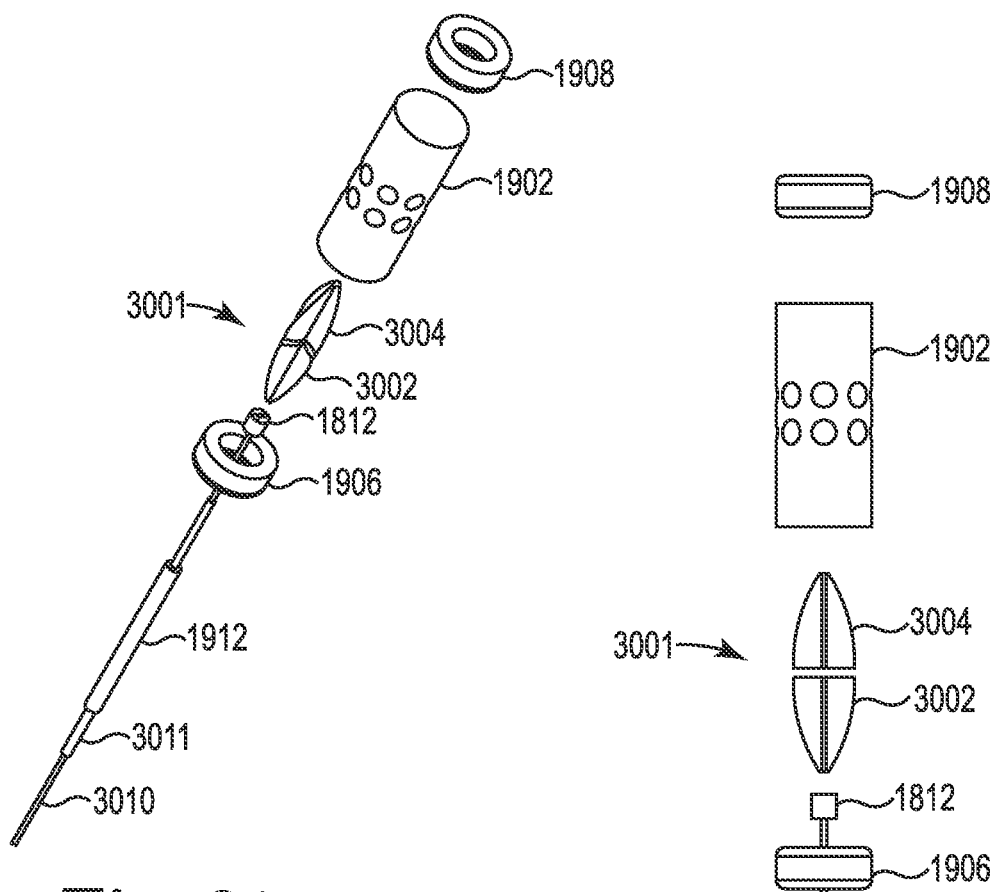
FIG. 31 is an exploded perspective view of an expandable blood pump according to one embodiment of the present disclosure.
Figure 32:
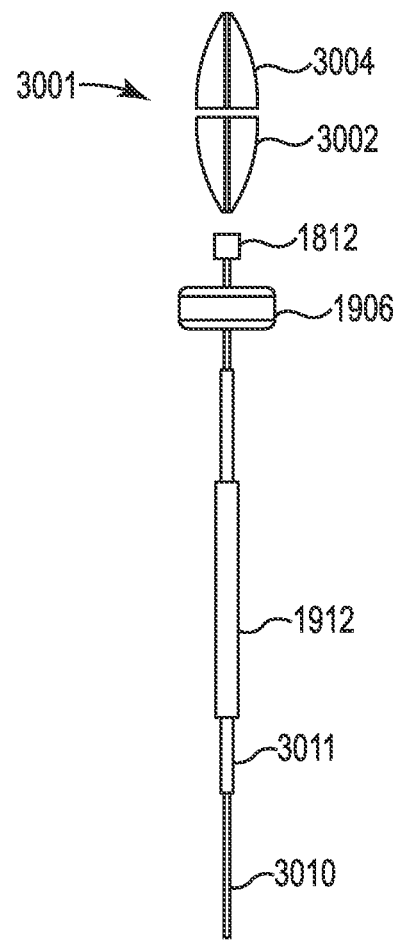
FIG. 32 is a side view of the expandable blood pump shown in FIG. 31.
Figures 33, 34:
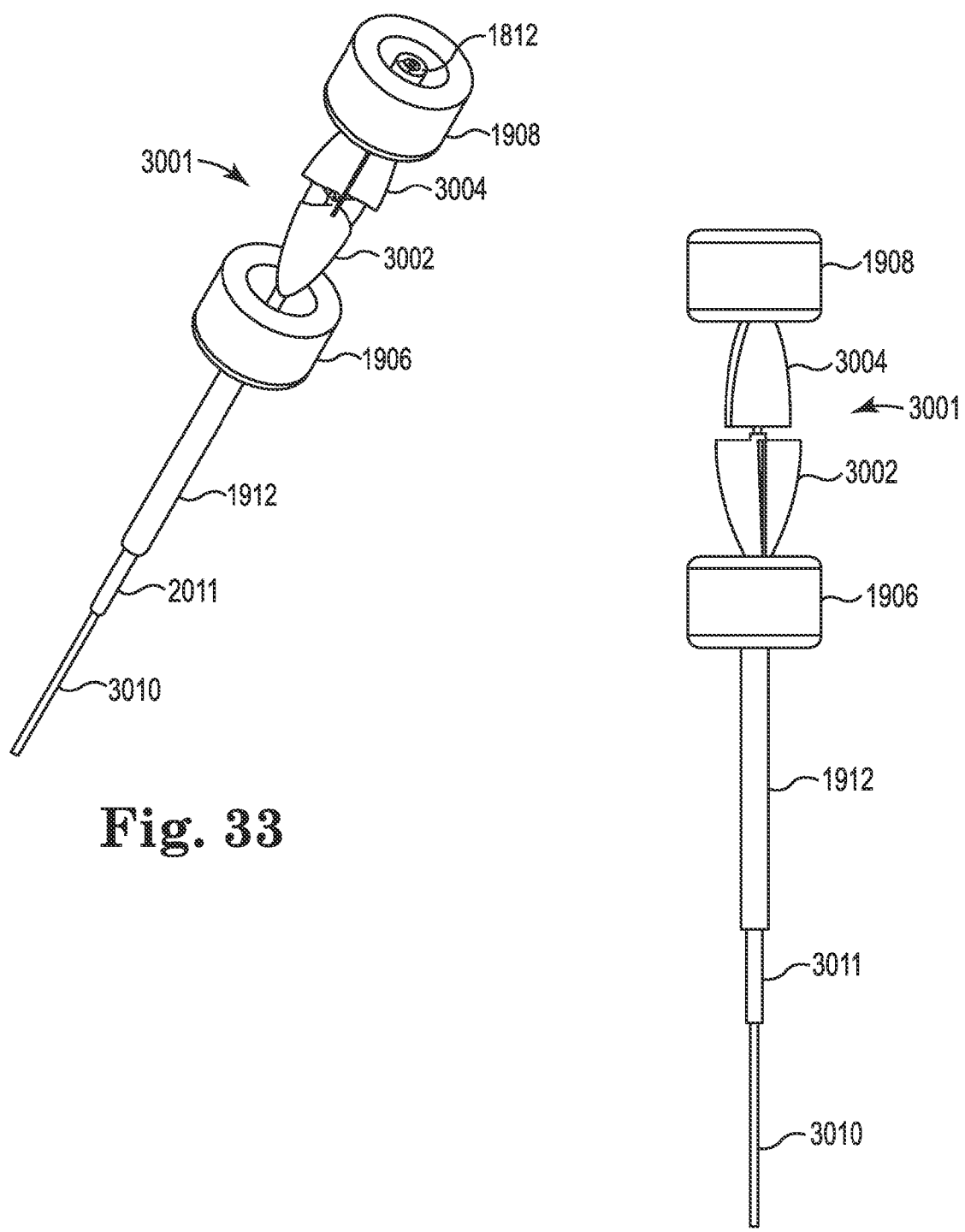
FIG. 33 is a perspective view of certain components of an expandable blood pump according to one embodiment of the present disclosure.
FIG. 34 is a side view of the certain components of an expandable blood pump shown in FIG. 33.

FIG. 30 depicts another embodiment of the expandable heart pump of the present invention, in which the impeller has more than one segment. The impeller 3001 of the expandable blood pump shown in FIG. 30 has two impeller segments, proximal impeller segment 3002 and distal impeller segment 3004. The various segments can be the same length, or different, and they can have the same diameter or different diameters. They can have the same number of blades, or different, and they can be made of the same or different materials. They also can be positioned similarly or differently as described above with respect to FIG. 29, and the gap between them can be adjusted as desired. Further, they can each have separate driveshafts 3010 and 3011, so that they can be independently controlled, if desired. All of these parameters can be adjusted, as desired, so that the desired blood flow, and the desired relative amounts of blood flow, from the inlets can be calibrated and selected. Any suitable number of impeller segments can be used. In one embodiment, three impeller segments are used, each with their own driveshafts. In one embodiment where three impeller segments are used, the center impeller segment is rotated at a greater number of revolutions per unit time than one or both of the other impeller segments, in order to generate greater blood flow in a lateral direction from the axis of rotation.

FIGS. 31-35 provide other views of an expandable heart pump of the present invention, with detail shown on types and various arrangements of components.

Figure 35:
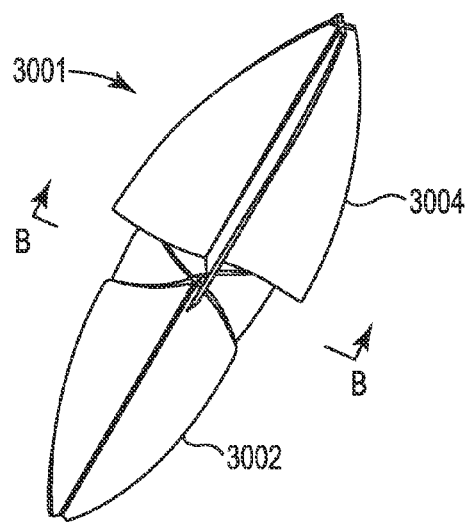
FIG. 35 is a perspective view of an impeller according to one embodiment of the present disclosure.
Figure 35A:
FIG. 35A is a cross-sectional view of the impeller of FIG. 35, taken along line B-B.
Figure 35B:
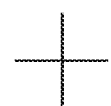
FIGS. 35B-35F depict cross-sectional views of other impellers of the present invention.
Figure 35C:
Figure 35D:
Figure 35E:
Figure 35F:

The shape and orientation of one or more impeller blades can be adjusted. As shown in FIG. 35, in one embodiment, the blades can have a slight curve. FIGS. 35B-35F depict cross-sectional views of other impellers of the present invention. As can be seen, any desired configuration can be used with any desired number of blades and any desired number of impeller segments.

The various embodiments of impellers of the present disclosure may include one or more impeller blades comprising a thin, flexible web or film of material. In some embodiments, the blades are suspended by or between one or more generally moveable, flexible, rigid or semi-rigid support members or masts. In other embodiments, the blades are made up of a material that does not use a support member or mast, such as where the blade is a collapsible, foldable, expandable, or inflatable section of polymer, web, a weave of wires, Nitinol or another memory metal, or another biologically suitable material, or a composite or combination of these. In some embodiments of impellers disclosed herein, the impeller may be activated between a collapsed, deployment configuration and an expanded, operable configuration by changing the position of the moveable, rigid or semi-rigid support members, thereby stretching the flexible web into a desired position and creating an impeller blade surface. In other embodiments of impellers disclosed herein, the impeller may be activated between a collapsed, deployment configuration and an expanded, operable configuration by changing the position of the blades, by inflating the impeller, by restraining the blades or allowing them to unfold or expand into their operable configuration of increased or maximum size, or by changing the relative proximal and distal positions (and length therebetween) of the pump. Thus, the impeller may permit a collapsed, deployment configuration of reduced or minimum size and an expanded, operable configuration of increased or maximum size.

As noted, the cannula may be supported by support members or ribs, as detailed above with regard to FIGS. 6 and 7. Guidance as described above with regards to FIGS. 12 and 13. Power transmission as described above in connection with FIGS. 14, 15, 16, and 17. In some embodiments of the present invention, the expandable blood pump may be provided within a sheath, as described above in connection with FIG. 14.

In some embodiments of the present invention, the expandable blood pump when used in a right heart configuration may include flow straighteners, as described above with respect to FIG. 9, which may take the form of a disk or flat member the plane of which is generally transverse to the expandable blood pump's axis of rotation. The flow straightener may be any desired shape, and may be aligned in any desired orientation. Where the flow straightener is used with a centrifugal pump, it may be provided as a flat ring, where the impeller is free to rotate within the center portion of the ring.

In further embodiments, as described above, one or more balloons or other expansion elements 654 may be provided outside of cannula 600, in order to secure pump 100 to a vascular feature such as a valve or aorta wall. Balloon elements 654 may expand by action of a biasing element, as described above, or through fluid pressurization, for example as provided by pump 100 or via an additional channel or lumen, for example as coupled to a fluid drive system, as described below.

A method of deploying and using an expandable blood pump according to the various embodiments described herein is described with reference to FIG. 36. As illustrated at step 3602, a catheter with a pump at or near the distal end thereof may be inserted into a major blood vessel and guided to the desired location, such as at the heart. The expandable blood pump may be inserted through a femoral artery, radial artery, subclavian artery, percutaneously, or by any other suitable passage or approach. One or more expandable members may be partially expanded to aid in insertion. In other embodiments, an additional expandable member may be used to help move the expandable blood pump to the desired location. Fluoroscopy, radiopaque markers, or other techniques may be used to further aid in positioning.

Once positioned, the expandable members can be expanded, so that they press against or engage surrounding vessel or other tissue. This helps to reduce or eliminate blood flow past the outside of the expandable blood pump, and to direct blood flow through the device, into the inlets. Expanding the expandable members can also help fully expand the device. The driveshaft turns, thus turning the impeller. The impeller's turning creates a pressure gradient between the inlets and the outlet, opening one or more heart valves, including the tricuspid and/or pulmonary values, thus creating blood flow, for example through the right heart. Pressure in the body may be measured by sensors as describe further herein. Flow through the inlets may be adjusted, and flow through each inlet may be adjusted relative to flow through the other inlet, as described herein, including by changing the pressure in or size of the expandable member, by varying the inlet size, by axially varying the impeller position relative to the two outlets, by varying the impeller diameter or configuration, by varying the impeller position, or by using an impeller with more than one segment and possibly varying the relative speeds of the segments.

As desired, additional tools or devices may be inserted through the catheter. Upon completion of the therapy, or when it is desirable to remove or reposition the expandable blood pump, it may be reoriented into a partially or fully collapsed configuration and then repositioned or removed.

As described in detail above, the pump may include an impeller and cannula, and the impeller and cannula may be initially inserted in a collapsed, deployment configuration. The impeller and cannula may be biased in the deployment configuration, or alternatively, may be retracted to the deployment configuration using a control unit operably coupled at or near the external end of the catheter. Once the pump is positioned in or near the desired location, e.g., desired chamber of the heart, at step 3604, the clinician or operator may use the control unit to adjust the pump's cannula, as described above, to an expanded, operable configuration, thereby creating a conduit for pump flow.

With the cannula expanded and a conduit created, at step 3606, the clinician or operator may adjust the pump's impeller within the cannula into its expanded, operable configuration. Although illustrated as separate steps 3604, 3606, in some embodiments, the adjustment of the cannula and impeller into their expanded, operable configurations may be done substantially simultaneously.

At step 3608, if desired, the impeller blade angle may be adjusted, as described in detail above for each of the various impeller embodiments, to create the desired pump flow direction. At step 3610, a power transmission system may be activated, for example using the control unit, to cause rotation of the impeller and generation of pump flow within the cannula between the cannula's inlet(s) and outlet(s). The clinician or operator may enter therapeutic system parameters into the control unit so as to drive the impeller at the desired speed. In general, the collapsed, deployment configuration may permit quick insertion to, and removal from, several anatomical positions while the expanded, operable configuration may permit appropriate therapy.

Another method of deploying and using an expandable blood pump according to the various embodiments described herein is described with reference to FIG. 37. As illustrated at step 3702, a catheter with a pump may be inserted into a major blood vessel and guided to the desired location, such as at the heart. The expandable blood pump may be inserted through a femoral artery, radial artery, or any other suitable passage. The pump may include an impeller and cannula, and the impeller and cannula may be initially inserted in a collapsed, deployment configuration. The impeller and cannula may be biased in the deployment configuration, or alternatively, may be retracted to the deployment configuration using a control unit operably coupled at or near the external end of the catheter.

Where the expandable blood pump is positioned within the right heart, it may be desirable to locate the proximal inlet of the expandable blood pump within the inferior vena cava and the distal inlet within the superior vena cava, as shown at step 3704.

At step 3706, the cannula is expanded, and at step 3708, the impeller is expanded. It is to be appreciated that some or all of these steps may be performed at the same time, or in a different sequence. For example, steps 3706 and 3708 may be done at the same time. Step 3704 may be done before or after one or both of steps 3706 and 3708.

At step 3710, a power transmission system may be activated, for example using the control unit, to cause rotation of the impeller and generation of pump flow within the cannula from the inlets through the side of the cannula, or between the cannula's inlet(s) and outlet(s). The clinician or operator may enter therapeutic system parameters into the control unit so as to drive the impeller at the desired speed. In general, the collapsed, deployment configuration may permit quick insertion to, and removal from, several anatomical positions while the expanded, operable configuration may permit appropriate therapy.

Figure 36:
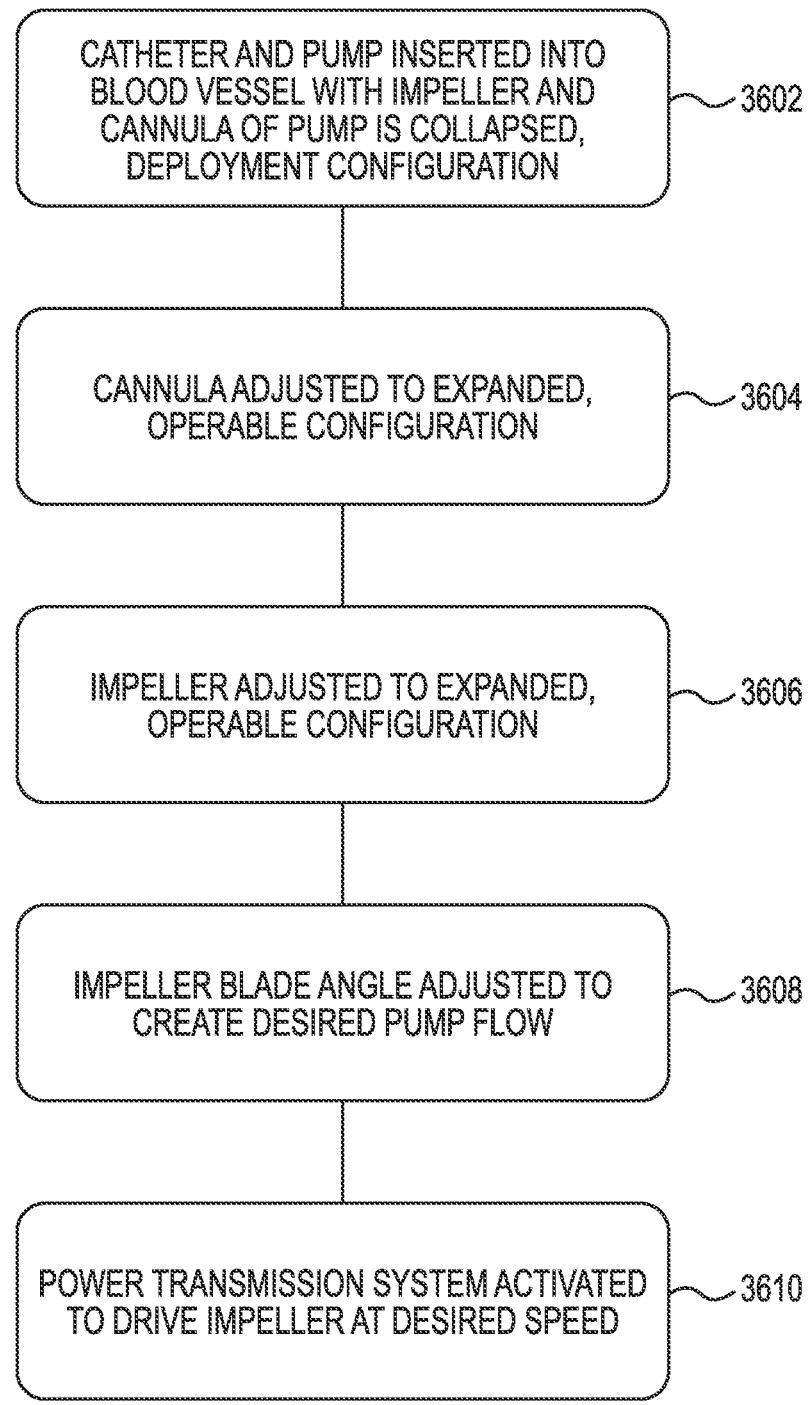
FIG. 36 is a flow diagram of a method of deploying and using an expandable blood pump according to one embodiment of the present disclosure.
Figure 37:
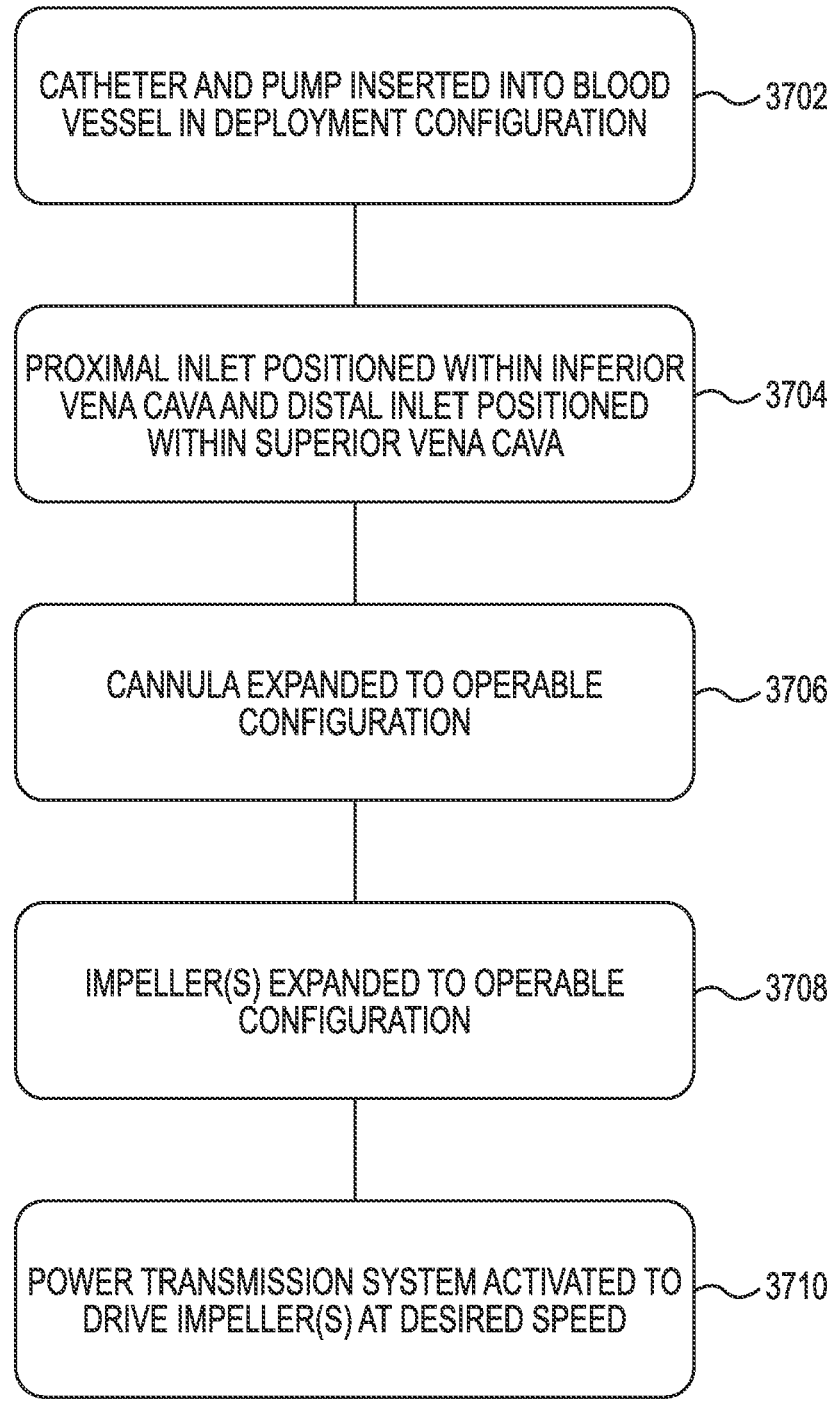
FIG. 37 is a flow diagram of another method of deploying and using an expandable blood pump according to one embodiment of the present disclosure.

In addition to the particular method steps described with respect to FIGS. 36 and 37, additional method steps may be included to perform one or more of the other functions described herein, including as depicted in any of the figures, with or without the steps shown in FIGS. 36 and 37.

Figure 38:
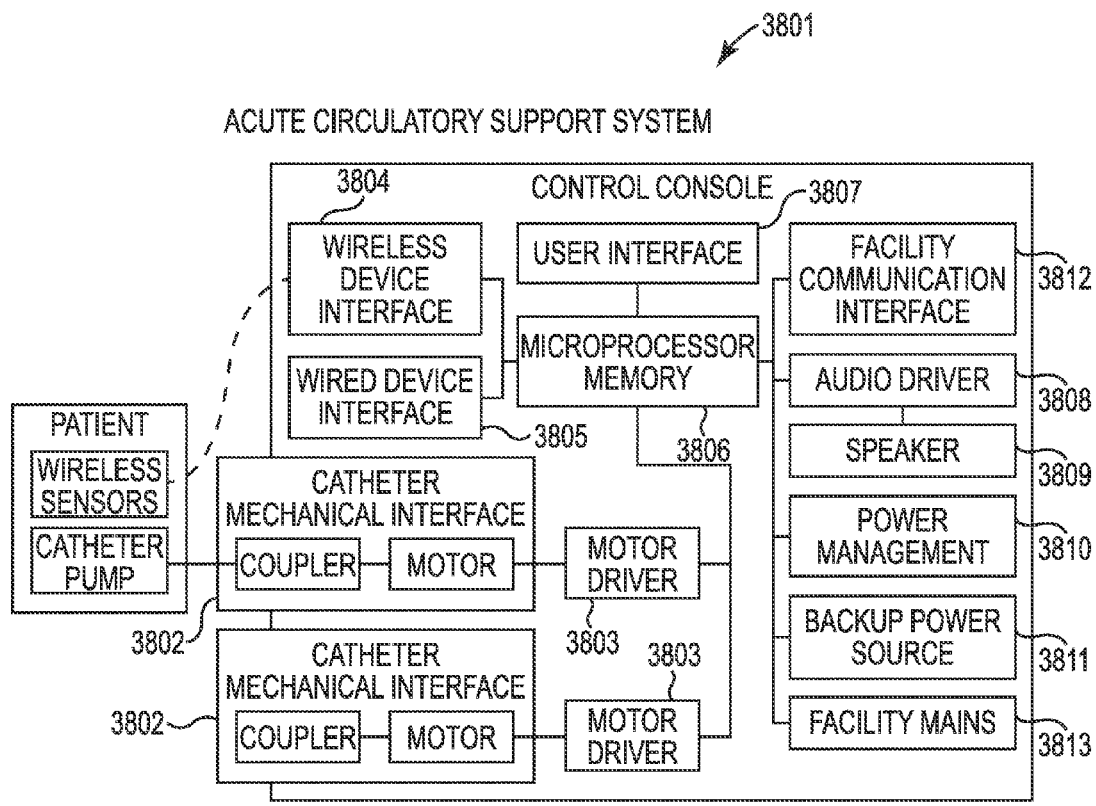
FIG. 38 is a schematic depiction of an expandable blood pump and a control system and console according to one embodiment of the present disclosure.

FIG. 38 depicts a control center 3801 for the expandable blood pump of the present invention. The control center 3801 can direct one or more pumps. The controller function can use a microprocessor and microprocessor memory 3806 to control the expandable blood pumps, such as based on one or more of predetermined algorithms, sensor feedback, and operator input. The control center 3801 may be adapted to coordinate with, communicate with, and/or direct sensors and other medical equipment, controllers, and monitors. Sensors may be positioned within the blood stream at various locations throughout the body to measure one or more of blood flow, blood pressure, temperature, oxygen content, and other parameters. Any suitable sensor or sensors may be used in any desired anatomical locations. In one embodiment, for example, pressure may be measured using a Swan-Ganz catheter. The sensors may be wireless 3804, or they may be wired 3805 to a control unit. The sensors may be operably connected to the expandable blood pump, or they may be separate, or a combination of these.

The control center 3801 has at least one catheter interface 3802. The catheter interface 3802 may be mechanical. In other embodiments, the catheter interface coupling can be magnetic, fluid, other, or a combination of these and mechanical, as described in further detail above. The pump may be operably connected to one or more interfaces. A drive 3803, which may be a motor driver 3803, may be provided that is operably connected to a driveshaft, such as via a coupler.

The control center 3801 may be controlled by an internal or external processor, such as through a program or other set of instructions. The control center 3801 may be adapted to be mounted on a pole, the patient, a bed stand, or other. The program or instructions may be provided in a stored memory, or on a memory device. The user interface 3807 may use one or more of audio, visual, and other signals and communication methods. Audio communication may be facilitated through an audio driver 3808 and one or more speakers 3809.

The control center 3801 may be powered by the facility power source, or facility mains 3813. The control center 3801 may have a module for power management 3810, and it may be provided with an internal or external backup power source 3811. Backup power source 3811 may be powered by battery, generator, other, or a combination. Power management module 3810 may control whether the control center 3801 is powered by facility mains 3818, backup power source 3811, other, or a combination of these.

There are many ways the control center 3801 may be used in operation. In one embodiment, a pump is deployed. A catheter of the expandable blood pump may be connected to the control center 3801, where the console recognizes the pump and prompts an operator for an appropriate input to start the pump. Additional pumps may be started in like fashion. The control center 3801 and/or the operator may configure various control parameters, such as impeller speed, maximum torque, alarm thresholds, and so on. Where more than one pump is used, the pumps may be operated independently, or the console may coordinate their operation, such as based on predetermined algorithms, sensor feedback, and/or operator input. The console may be used to coordinate operation for various medical devices and equipment. In one embodiment, the console may provide a single control interface for setting the speed for circulatory support, a bypass, and/or the catheter pump. This may assist in transitioning a patient from the support of the blood pump to the long term support of another device.

The control center 3801 can incorporate multiple wired or wireless sensor datastreams, such as into an algorithm. If the pump incorporates electrodes, the control center 3801 may be used to sense and pace based on the input it receives. The control center 3801 would be able to transfer patient and machine data to the facility database. The control center 3801 may have a facility communication interface 3812.

The control center 3801 is capable of operating multiple pumps, of identifying and controlling pumps, of providing an interface (which may be wireless) with a console, and communicating with, coordinating with, and/or controlling other devices.

Although the various embodiments of the present disclosure have been described with reference to preferred embodiments, persons skilled in the art will recognize that changes may be made in form and detail without departing from the spirit and scope of the present disclosure. In particular, various elements of the figures may be interchanged or combined to form different groupings and arrangements of features, without loss of generality. For example, each of the cannula, impeller, rib, support member, catheter, web, blade, mast and other features, as shown in the different figures and as described using various reference numbers in the specification, may be interchanged or combined according to different embodiments of the invention, and adapted to different applications, functions and materials, while remaining within the spirit and scope of the invention, as encompassed by the following claims.

The invention claimed is:

1. A pump for inducing flow within a vascular system, comprising:
   at least one inlet; and
   an impeller configured to induce the fluid flow by rotation about an axis, wherein said fluid flow is in a direction generally transverse to the axis;
   wherein said impeller has a first configuration for deployment within the vascular system and a second configuration for directing the fluid flow within the vascular system, the second configuration having a greater diameter than the first configuration.

2. The pump of claim 1, comprising at least two inlets.

3. The pump of claim 1, comprising an expandable member at the at least one inlet.

4. The pump of claim 3, wherein said expandable member contains a selectively adjustable aperture.

5. The pump of claim 3, wherein said impeller has at least two segments.

6. The pump of claim 5, wherein each impeller segment is independently controllable.

7. The pump of claim 2, wherein said impeller has an axially adjustable position.

8. The pump of claim 3, comprising an expandable member at each of the at least two inlets.

9. The pump of claim 8, wherein each expandable member has a selectively adjustable aperture.

10. The pump of claim 3, wherein the expandable member has a length that is axially adjustable.

11. The pump of claim 2, wherein the pump has an axially adjustable length.

12. The pump of claim 4, wherein said impeller has an expandable core region.

13. A pump for inducing flow within a vascular system, comprising:
    at least two inlets;
    a cannula; and
    an impeller configured to induce the fluid flow by rotation about an axis;
    wherein said impeller has a first configuration for deployment within the vascular system and a second configuration for directing the fluid flow within the vascular system, the second configuration having a greater diameter than the first configuration; and
    wherein said cannula has a first configuration for deployment within the vascular system and a second configuration for directing the fluid flow within the vascular system, the second configuration having a greater diameter than the first configuration.

14. The pump of claim 13, wherein said fluid flow is in a direction generally transverse to the axis.

15. The pump of claim 13, comprising an expandable member at each inlet.

16. The pump of claim 15, wherein each expandable member has a selectively adjustable aperture.

17. The pump of claim 15, comprising a catheter extending to a proximal end of the cannula, wherein the catheter is configured to position the cannula within the vascular system.

18. The pump of claim 14, wherein said cannula contains a plurality of lateral openings.

19. The pump of claim 16, wherein said impeller has at least two segments.

20. The pump of claim 16, wherein said impeller has blades with an arcuate profile.

* * * * *